(12) United States Patent
Travanty

(10) Patent No.: US 9,789,257 B2
(45) Date of Patent: *Oct. 17, 2017

(54) NEEDLE ASSISTED INJECTION DEVICE HAVING REDUCED TRIGGER FORCE

(71) Applicant: Antares Pharma, Inc., Ewing, NJ (US)

(72) Inventor: Michael Travanty, S. Minneapolis, MN (US)

(73) Assignee: Antares Pharma, Inc., Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/418,659

(22) Filed: Jan. 27, 2017

(65) Prior Publication Data

US 2017/0136184 A1    May 18, 2017

Related U.S. Application Data

(63) Continuation of application No. 14/178,199, filed on Feb. 11, 2014.

(60) Provisional application No. 61/776,283, filed on Mar. 11, 2013, provisional application No. 61/763,395, filed on Feb. 11, 2013.

(51) Int. Cl.

| | |
|---|---|
| *A61M 5/20* | (2006.01) |
| *A61M 5/30* | (2006.01) |
| *A61M 5/32* | (2006.01) |
| *A61M 5/50* | (2006.01) |
| *A61K 9/00* | (2006.01) |
| *A61K 31/57* | (2006.01) |

(52) U.S. Cl.
CPC ............ *A61M 5/30* (2013.01); *A61K 9/0019* (2013.01); *A61K 31/57* (2013.01); *A61M 5/2033* (2013.01); *A61M 5/3204* (2013.01); *A61M 5/326* (2013.01); *A61M 5/3245* (2013.01); *A61M 5/3257* (2013.01); *A61M 5/5086* (2013.01); *A61M 2005/2013* (2013.01); *A61M 2005/2073* (2013.01); *A61M 2005/3247* (2013.01); *A61M 2205/584* (2013.01)

(58) Field of Classification Search
CPC ............ A61M 5/24; A61M 2005/2407; A61M 5/2033; A61M 5/31585

See application file for complete search history.

(56) References Cited

PUBLICATIONS

Office Action for Japanese Patent Application No. 2015-557208.

*Primary Examiner* — Aarti B Berdichevsky
(74) *Attorney, Agent, or Firm* — Morgan, Lewis & Bockius LLP

(57) ABSTRACT

An injector includes a trigger mechanism including: a trigger member disposed about an axis having an aperture and a protrusion, and a ram assembly having a ram configured to pressurize a medicament container for expelling a medicament therefrom, the ram assembly further having a trigger engagement member configured to engage the aperture of the trigger member when the trigger member is in a pre-firing condition; an energy source associated with the ram for powering the ram to expel the medicament; and a user-operable firing-initiation member having an aperture engaged with the protrusion of the trigger member and operable for causing an axial translation of the trigger member in a proximal direction from the pre-firing condition to a firing condition in which the trigger engagement member is released from the retaining portion to allow the energy source to fire the ram.

15 Claims, 26 Drawing Sheets

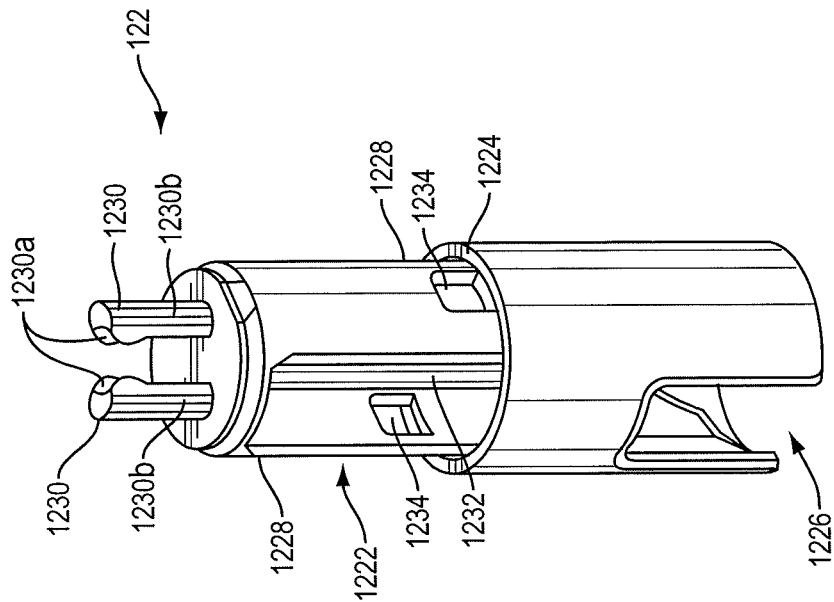
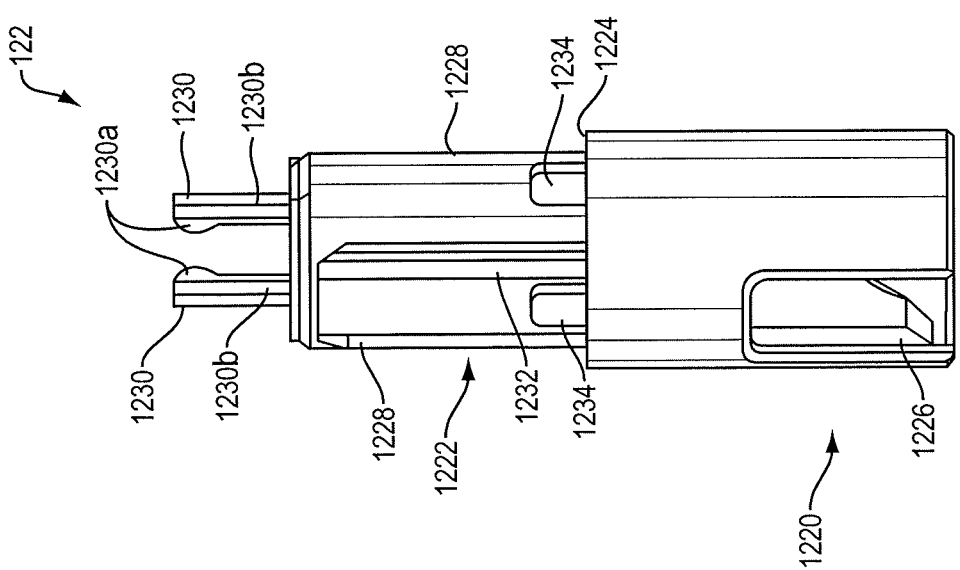

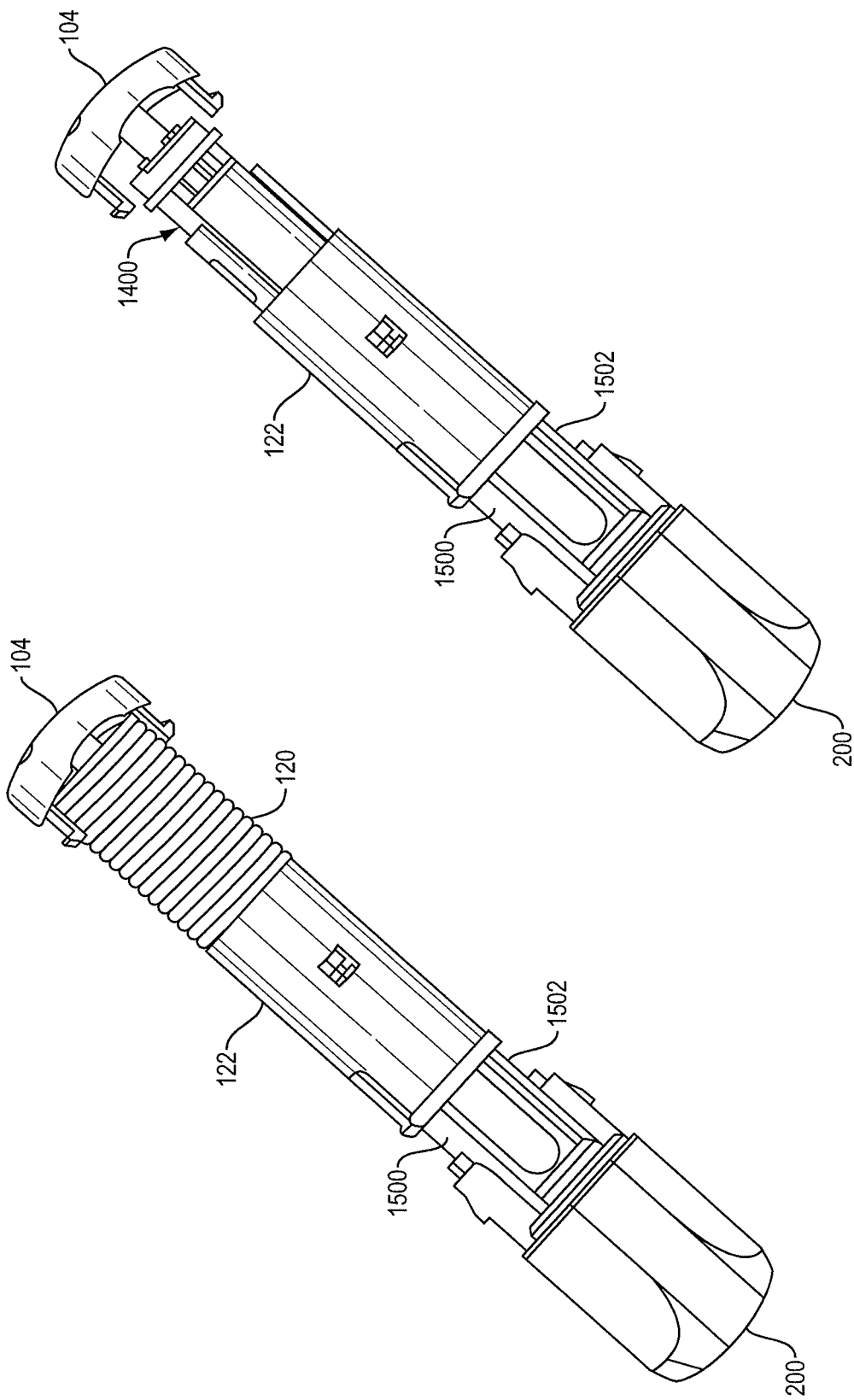

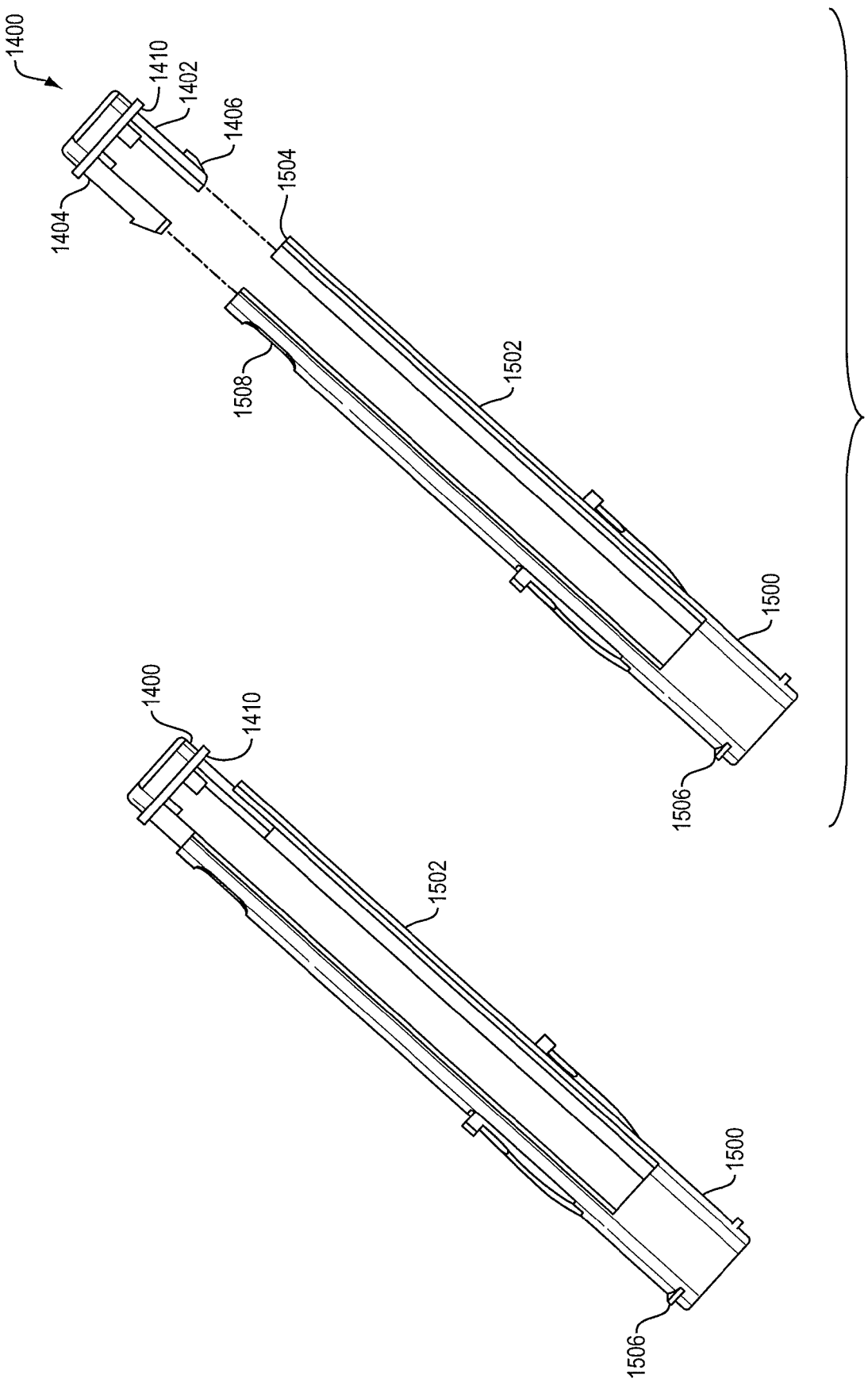

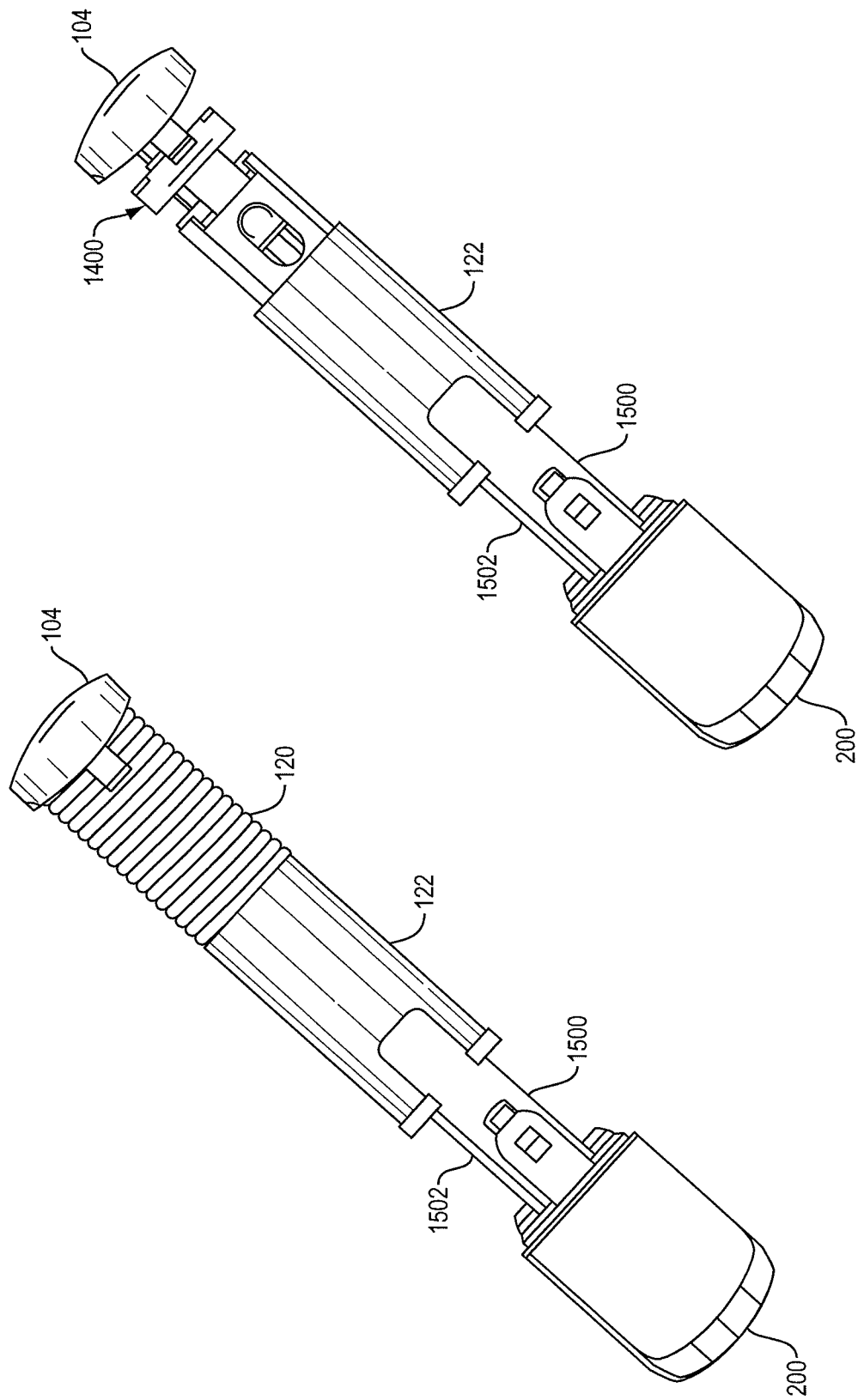

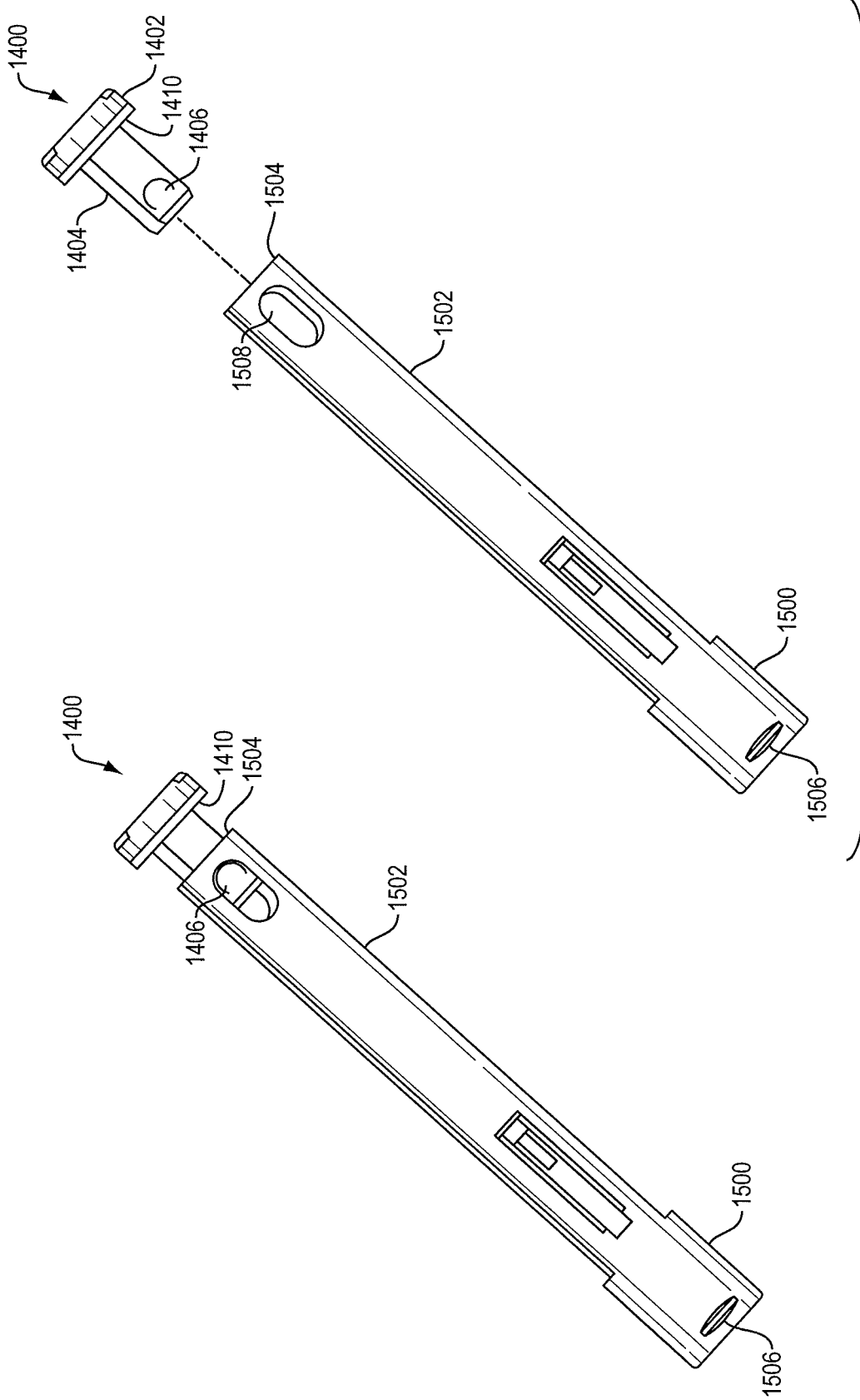

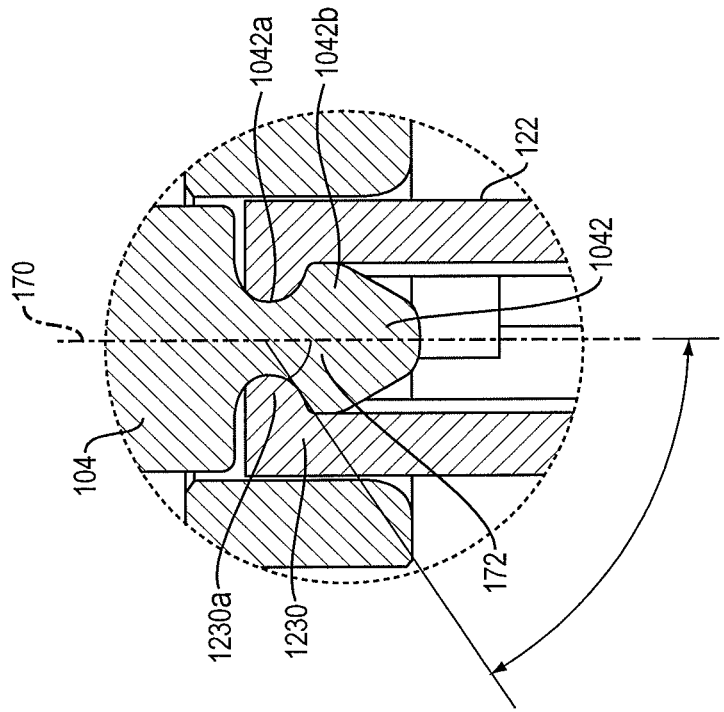
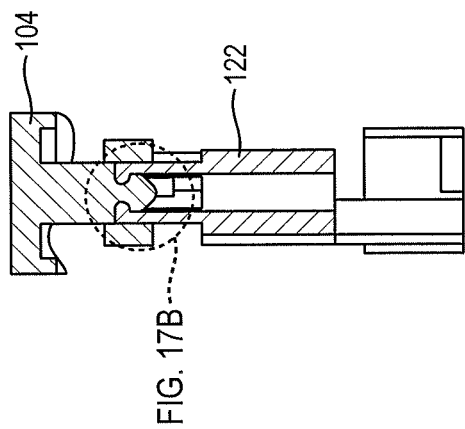

NEEDLE ASSISTED INJECTION DEVICE HAVING REDUCED TRIGGER FORCE

CROSS-REFERENCE TO RELATED APPLICATIONS

This application is a continuation of U.S. patent application Ser. No. 14/178,199, filed Feb. 11, 2014, which in turn claims the benefit of and priority to U.S. Provisional Application No. 61/763,395 filed Feb. 11, 2013, and U.S. Provisional Application No. 61/776,283, filed Mar. 11, 2013.

FIELD OF THE DISCLOSURE

The present disclosure relates to injection devices, and in some embodiments a needle assisted jet injector for special medicaments such as testosterone or midazolam.

BACKGROUND INFORMATION

Various injection devices exist that employ an automated mechanism to actuate injection of a liquid medicament into a patient. Examples of such devices include jet injectors (both needle-free and needle-assisted) and traditional, low-pressure auto-injectors (that provide, for example, mechanized delivery of a traditional, finger-powered hypodermic syringe injection). Although the precise mechanisms used to complete an injection can vary, most include a feature that stores kinetic energy that can be used to drive an injection mechanism during use. Further, many injectors include a trigger mechanism configured to ensure that the kinetic energy remains stored until an injection is desired, whereby actuation of the trigger releases the injection mechanism, allowing the stored kinetic energy to drive the injection mechanism to cause injection.

Examples of needle-free jet injectors are described, for example, in U.S. Pat. Nos. 5,599,302 and 4,790,824. These high force injectors are button activated and administer medication as a fine, high velocity jet delivered under sufficient pressure to enable the jet to pass through the skin. The injection mechanism in such needle-free jet injectors can apply a force to a medicament storing chamber within the device such that the pressure required to inject the medicament is created within the chamber.

Traditional self-injectors or auto-injectors like the ones described, for example, in U.S. Pat. Nos. 4,553,962 and 4,378,015 and PCT Publication WO/9714455 inject medicament at a rate and in a manner similar to hand-operated hypodermic syringes. The described self-injectors or auto-injectors have needles that are extended at the time of activation to penetrate the user's skin to deliver medicament through movement of the drug container and related needle. Thus, the mechanism that provides the force to deliver the medicament in traditional, low-pressure self-injectors and auto-injectors can also be used to extend the needle and displace the drug container to cause the insertion of the needle through the user's skin and to apply a force to a plunger movably disposed within the drug container to cause the medicament to be expelled from the container through the needle. The auto-injectors manufactured, for example by Owen Mumford, thus use very low pressures to inject the medicament, which is typically injected through a needle in a relatively slow stream. Another self-injector includes the Simponi injector, which includes a window in the housing through which a yellow ram is visible inside a clear medicament container once the injector has been used.

Additionally, needle-assisted jet injectors have also been developed with higher injection forces that utilize a needle to initially penetrate the skin allowing a range of needle insertion depth at times less than that of a traditional hypodermic injector or low-pressure auto-injectors. Once the skin is penetrated with the needle, a jet mechanism is activated, causing the medicament containing liquid within the injector to be pressurized and expelled through the needle and into the skin. The injection mechanism in needle-assisted jet injectors can be configured to move the drug container and the needle forward to penetrate the skin and exert the necessary injection force to a plunger moveably disposed within the container. Alternatively, the needle and drug container can be positioned to penetrate the skin while keeping the needle and drug container in a stationary position, and the injection mechanism can be structured to pressurize the container. The pressure applied to the medicament within the injector can be less than that of a traditional jet injector, because the outer layers of the skin have already been penetrated by the needle. Similarly, the pressure applied to the medicament is preferably higher than that of a traditional auto-injector or the like, causing the medicament to penetrate the skin and be dispersed into the tissue or injected in the tissue below the skin to a depth that is sufficient so that the medicament remains substantially within the body. An additional benefit of the higher pressure includes a faster time of injection resulting in less psychological trauma to the patient and a decreased likelihood of the user inadvertently terminating the injection prematurely by removing the injector from the injection site.

Because of the stored energy associated with the trigger and injection mechanisms, accidental firing can occur due to sudden movements during shipping or due to mishandling of the device by a user including accidental actuation of the trigger mechanism. Accidental firing of the injection mechanism can cause the medicament to be expelled from the device, which can be at a dangerously high pressure, depending on the type of injection device. Further, accidental firing can cause an injection needle to move forward with respect to the device with sufficient force to penetrate the skin.

Additionally, the dimensions of many components incorporated in injectors typically constrain the design of many injectors. For example, many injectors utilize front firing-initiation mechanisms that typically require an axial translation and engagement with a triggering structure located at the back of the injector. However, this configuration typically promotes binding of the communicating triggering components due to but not limited friction between components in slidable communication and component distortion, which can be advantageous for, e.g., reducing the size of the injection device, being able to view the drug container within the device, etc.

SUMMARY

In one embodiment of the invention, the invention relates to an injector. In one embodiment, the invention is an injector including a trigger member disposed about an axis having an aperture and a protrusion, and a ram assembly having a ram configured to pressurize a medicament container for expelling a medicament therefrom, the ram assembly further having a trigger engagement member configured to engage the aperture of the trigger member when the trigger member is in a pre-firing condition; an energy source associated with the ram for powering the ram to expel the medicament; and a user-operable firing-initiation member having an aperture engaged, either slidingly or directly, with the protrusion of the trigger member and operable for causing an axial translation of the trigger member in a proximal direction from the pre-firing condition to a firing condition in which the trigger engagement member is released from the retaining portion to allow the energy source to act on the ram.

In one embodiment, the injector further includes an injector housing, wherein the firing initiation member includes a skin-contacting member disposed at a distal end of the injector that is movable proximally with respect to the housing when a force is applied to the skin-contacting member at the distal end of the injector, the firing initiation member being associated with the trigger member and configured to cause the axial translation of the trigger member in a proximal direction from the pre-firing condition to the firing condition upon a proximal movement of the skin-contacting member with respect to housing.

In one embodiment, the skin-contacting member includes a needle guard that is retractable and is configured to expose a needle connected to the medicament container upon the proximal movement of the skin-contacting member.

In one embodiment, the needle is in fluid communication with the medicament container for injecting the medicament expelled therefrom during the firing.

In one embodiment, the energy source and the needle are configured for jet injecting the medicament through the needle.

In one embodiment, the energy source is configured to pressurize the medicament to between about 90 p.s.i. and about 600 p.s.i. to jet inject the medicament.

In one embodiment, the energy source and needle are configured for injecting the medicament at an average velocity of at least about 1,000 cm/sec within the needle.

In one embodiment, the injector further includes an end cap, said end cap comprising a ram holding member that axially retains the ram assembly in a proximal position against action of the energy source in the pre-firing position.

In on embodiment, the ram holding member engages the trigger engagement member to axially retain the ram assembly in a proximal position against action of the energy source in the pre-firing position.

In one embodiment, the injector includes a latch retention angle defined by the axis and a contact surface of the ram holding member and the trigger engagement member. In some embodiments, the latch retention angle is between about 35° and about 45°. In other embodiments, the latch retention angle is between about 75° and about 85°.

In one embodiment, in the firing condition, the ram is disengaged from the aperture, and the energy source overcomes the engagement between the trigger engagement member and the ram holding member.

In one embodiment, the ram holding member includes a projection that includes a bulge and a groove that are engaged with the trigger engagement member, and the aperture of the trigger member retains the engagement of the trigger engagement member with the bulge and groove in the pre-firing condition.

In one embodiment, the injector further includes a container support that is configured for holding the medicament container during injection, and wherein the ram assembly is configured to engage the container support to lock-out the injector after an injection.

In one embodiment, proximal movement of the user-operable firing-initiation member is blocked by the ram assembly when the injector is locked-out.

In one embodiment, a pre-firing color gamut is visible from the exterior of the injector in the pre-firing condition, the injector further including: a housing including a window; and an indicator having an indicator color that is absent from the pre-firing color gamut, which color is hidden from view within the housing in the pre-fired condition, wherein in the fired condition, the indicator color is visible through the window from an exterior of the injector for indicating the fired condition. In certain embodiments, the ram assembly includes the indicator. In some embodiments, the ram assembly entirely occludes the window in the fired condition.

In one embodiment, the medicament comprises an androgen. In other embodiments, the androgen includes testosterone or a derivative or ester thereof. In certain embodiments, the androgen includes testosterone cypionate. In one embodiment, the androgen includes testosterone enanthate. In one embodiment, the medicament comprises a midazolam.

In one embodiment, the aperture of the firing-initiation member is slidingly engaged with the protrusion of the trigger member.

In one embodiment, the ram assembly is of unitary construction.

BRIEF DESCRIPTION OF THE DRAWINGS

These and other objects, features and advantages of the invention will be apparent from a consideration of the following non-limiting detailed description considered in conjunction with the drawing figures, in which:

FIGS. 10A and 10B are side and perspective views of a ram assembly of an exemplary injection device according to an exemplary embodiment of the present disclosure;

FIGS. 15A and 15B are side views of a ram assembly, needle guard, housing end/end cap, and trigger member of an exemplary injection device according to an exemplary embodiment of the present disclosure;

FIGS. 15C and 15D are side views of a needle guard and trigger member of an exemplary injection device according to an exemplary embodiment of the present disclosure;

FIGS. 15E and 15F are side views of a ram assembly, needle guard, housing end/end cap, and trigger member of an exemplary injection device according to an exemplary embodiment of the present disclosure;

FIGS. 15G and 15H are side views of a needle guard and trigger member of an exemplary injection device according to an exemplary embodiment of the present disclosure;

FIG. 17A is a cross-section view of a portion of the end cap, ram assembly and trigger as shown in FIG. 16A;

FIG. 17B is a magnified cross-section view of a portion of the end cap, ram assembly and trigger as shown in FIG. 17A;

Figure 1:
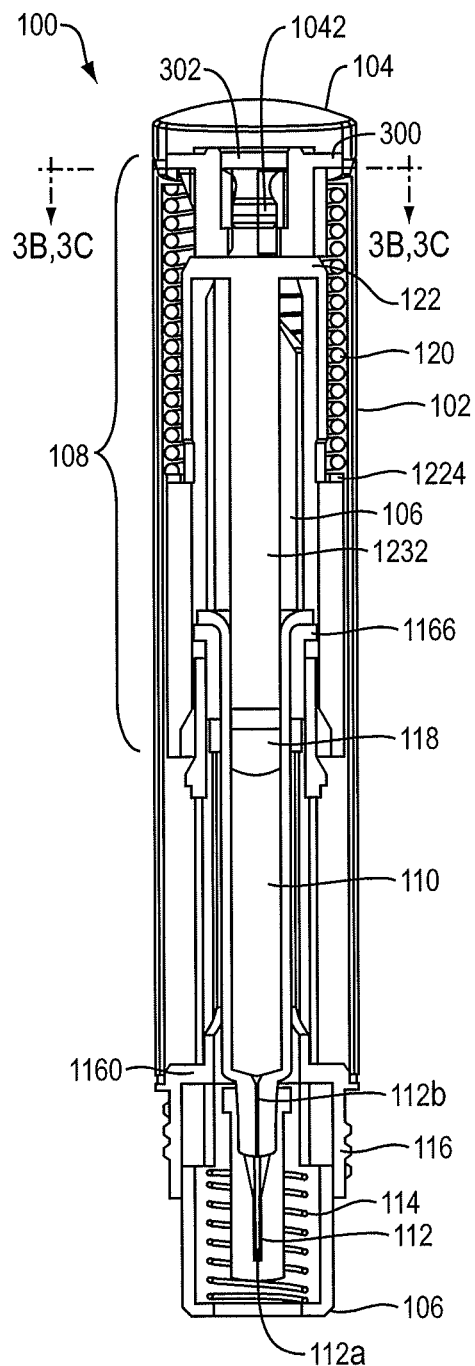
FIG. 1 is a cross-sectional view of an exemplary injection device according to an exemplary embodiment of the present disclosure.

Throughout the figures, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

With reference to the accompanying figures, various embodiments of the present invention are described more fully below. Some but not all embodiments of the present invention are shown. Indeed, various embodiments of the invention may be embodied in many different forms and should not be construed as limited to the embodiments expressly described. Like numbers refer to like elements throughout. The singular forms "a," "an," and "the" include the singular and plural unless the context clearly dictates otherwise.

FIG. 1 shows an exemplary injection device 100 according to an exemplary embodiment of the present disclosure. It is noted that, in the context of this disclosure, the terms "distal" and "proximal" are used in reference to the position of the injection device relative to a user of the injection device when held by a user. Accordingly, a point located distal to a second point would be further from the user (i.e., towards an injection end of the injection device) and vice versa. As shown in the drawings, an exemplary injection device 100 is a needle assisted jet injection device, although a person having ordinary skill in the art will understand alternative embodiments employing certain features herein can be configured as needle-free jet injectors, or as low-pressure auto-injectors or other mechanized injectors. According to certain exemplary embodiments, injection device 100 is a one-time disposable needle-assisted jet injector. In certain embodiments, injection device 100 can be modified to provide multiple and/or variable dosings upon repeated injections. According to certain exemplary embodiments, injection device 100 is a one-time disposable needle-assisted jet injector with a lock-out feature. For example, injection device 100 can facilitate a jet injection of medicament stored within injection device 100 and can include a locking feature that prevents a user from attempting to use injection device 100 once the medicament has been dispensed. In one embodiment, the locking feature is activated upon dispensing of the medicament and not upon use of injection device 100. For example, the locking feature can be activated, thus preventing injection device 100 from a subsequent attempted use by a user, even in the case where the injection device was not actually used by a user for an injection, but where a firing mechanism was inadvertently activated (e.g., during transport, handling, etc. of the device) and the medicament was dispensed. Operation of injection device 100, including the locking feature, is described in further detail below.

According to certain exemplary embodiments, injection device 100 can deliver any suitable liquid drug or medicament. Further, injection device 100 can allow the injection to be administered by individuals that do not have formal training (e.g., self-administered or administered by another individual family member or other caregiver who may not be a formally trained healthcare provider, such as a parent administering a drug to a child). Accordingly, injection device 100 can be useful in situations where self-injections/caregiver administered injections would be beneficial, including, but not limited to, inflammatory diseases, low testosterone also known as low T, hypogonadism, diabetes, infertility treatment, sexual dysfunction, cardiovascular disease, oncology, oncology supportive care, allergic reaction, multiple sclerosis, rheumatoid arthritis psoriasis, other autoimmune conditions including Crohn's disease and systemic lupus erythematosus (SLE), chronic pain, migraine, acute seizure, epileptic seizure, kidney disease, and the like. Further, injection device 100 can be used to inject a wide range of drugs. For example, injection device 100 can be used to inject drugs, water soluble medicaments, peptides, proteins, depot formulations and oil soluble medicaments. In one embodiment, the medicament includes a benzodiazepine, including midazolam. In another embodiment, the medicament is dissolved in oil instead of aqueous solutions, and can include hormone drugs used in men (e.g., testosterone, or a derivative or ester thereof) and women; small molecule injectable drugs such as, methotrexate (see, e.g., International Publication No. WO 2010/108116, which is incorporated by reference herein in its entirety); and/or biological drugs, including those having a high viscosity. Further, and as noted above injection device 100 can be used to inject androgens, including testosterone formulations (e.g., testosterone cypionate and testosterone enanthate). In certain embodiments, injection device is designed to enhance the administration and performance of complex and difficult to inject viscous medicines, such as but not limited to testosterone, biologics or biosimilars. In one embodiment, the injection device is designed to cause a powerful and smooth expulsion of a medicament, which may be necessary for viscous formulations, including but not limited to biologics.

Testosterone is a steroid hormone from the androgen group. In general, androgens promote protein synthesis and growth of those tissues with androgen receptors. Testosterone is anabolic, meaning it builds up bone and muscle mass. Testosterone has the following structural formula:

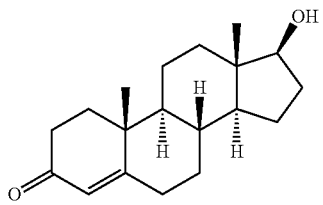

The original and primary use of testosterone is for the treatment of males who have too little or no natural endogenous testosterone production—males with Low T or hypogonadism. According to the Massachusetts Male Aging Study, about 6% to 12% men aged 40 to 60 years have symptomatic low testosterone deficiency. However, over the years, testosterone has also been given for many other conditions, e.g., reducing infertility, correcting lack of libido or erectile dysfunction, correcting osteoporosis, encouraging penile enlargement, encouraging height growth, encouraging bone marrow stimulation, reversing the effects of anemia and appetite stimulation.

In certain embodiments, injection device 100 can be used to inject one or more of epinephrine, atropine, dihydroergotamine, sumatriptan, antibiotics, antidepressants, anticoagulants, glucagon, diazepam, haloperidol, apomorphine, lovenox, and toradol. In other embodiments, injection device 100 can be used to inject biosimilar, biological and or peptide drugs, including without limitation Enbrel, Humira, Lantus, Epogen (Procrit), Neulasta, Aranesp, Avonex, PEGasys, Rebif, Neupogen, Betaseron, Avastin, Remicade, Herceptin, Erbitux, Recombinate, Cerezyme, NovoSeven, Tysabri, Synagis, Copaxone and Kogenate FS.

In other embodiments, injection device 100 can be used to inject parathyroid hormone ("PTH") and various other medications such as exenatide and the like. Injection device 100 can also be used to inject medicaments listed in the Physicians' Desk Reference (PDR®), 67th Edition (2013) (which is herein incorporated by reference in its entirety), and, without limitation, allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antiviral antibiotics, anticancer preparations, anticholinergic drug inhibitors, anticoagulants, anticonvulsants, antidiabetic agents, antidiarrheals, antidiuretics, antienuresis agents, antifibrinolytic agents, antifibrotics (systemic), antiflatulents, antifungal agents, antigonadotropin, antihistamines, antihyperammonia agents, anti-inflammatory agents, antimalarials, antimetabolites, antimigraine preparations, antinauseants, antineoplastics, anti-obesity preparations, antiparasitics, anti-parkinsonism drugs, antipruritics, antipyretics, antispasmodics and antichloinergics, antitoxoplasmosis agents, antitussives, antivertigo agents, antiviral agents, biologicals, biosimilars, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, cough and cold preparations, decongestants, diazepam, epinephrine expectorants and combinations, diuretics, emetics, enzymes and digestants, fertility agents, fluorine preparations, galactokinetic agents, general anesthetic, geriatrics, germicides, hematinics, hemorrhoidal preparations, histamine H receptor antagonists, hormones, hydrocholeretics, hyperglycemic agents, hypnotics, immunosuppressives, laxatives, mucolytics, muscle relaxants, narcotic antagonists, narcotic detoxification agents, ophthalmological osmotic dehydrating agents, otic preparations, oxytocics, parashypatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics, thrombolytics, thyroid preparations, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the PDR®. Some other medicaments that can be used with injector device 100 include Ergocalciferol (Calciferol), diethylstilbestrol, Diprovan (propofol), estradiol valerate, fluphenazine decanoate, fulvestrant, intralipid, liposyn, nandrolone decanoate, nebido, nutralipid, paclitaxel, progesterone, prograf, testosterone cypionate, zuclopenthixol, and haloperidol dodecanoate. In certain embodiments, the medicament is dissolved in soybean oil, ethyl oleate, castor oil, sesame oil, safflower oil, arachis oil, polyoxyyethylated castor oil (Cremophor® EL), polyoxyl 60 hydrogenated castor oil (HCO-60), cottonseed oil, or thin oil derived from coconut oil.

In some embodiments, the medicament may be a hazardous agent. "Hazardous Agent(s)" as used herein means any one or more medications that are toxic agents, cytotoxic agents and/or other dangerous agents that may cause serious effects upon contact with a subject as well as highly potent agents, agents that have profound physiological effects at low doses. Exemplary hazardous agents include, without limitation, analgesics, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. Examples of hazardous agents suitable for use with injection device 100 in accordance with the present invention include, but are not limited to, those disclosed in U.S. Patent Application Publication No. 2012/0157965 entitled "Hazardous Agent Injection System" (to Paul Wotton et. al, published Jun. 21, 2012), which is incorporated by reference herein in its entirety. Particular examples of cytotoxic agents include, without limitation, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, and derivatives thereof. Examples of highly potent agents include, without limitation, steroids such as dexamethasone, progesterone, somatostatin, and analogues thereof; biologically active peptides such as teriparatide; and anticholinergics such as scopolamine. Examples of agents that have profound physiological effects at low doses include, without limitation, antihypertensives and/or blood pressure down regulators. Examples of analgesics include, without limitation, fentanyl, fentanyl citrate, morphine, meperidine, and other opioids. Examples of immunomodulating agents include, without limitation, adalimumab (anti-tissue necrosis factor monoclonal antibody or anti-TNF). Examples of IL-1 receptor antagonists include, without limitation, anakinra. Examples of IL-2 alpha receptor antagonists include, without limitation, daclizumab and basiliximab. Examples of anti-rejection compounds include, without limitation, azathioprine, cyclosporine, and tacrolimus. Examples of hormonal agents include, without limitation, testosterone, estrogen, growth hormone, insulin, thyroid hormone, follicle stimulating hormone (FSH), epinephrine/adrenaline, progesterone, parathyroid hormone, gonadotrophin releasing hormone (GHRH), leutinizing hormone releasing hormone (LHRH), other hormones such as those where contact with the hormone by members of the opposite sex can lead to side effects, and derivatives thereof. Examples of prostaglandins include, without limitation, gamma-linolenic acid, docosahexanoic acid, arachidonic acid and eicosapentaenoic acid. Examples of sedatives include, without limitation, barbiturates such as amobarbital, pentobarbital, secobarbital, and phenobarbitol; benzodiazepines such as clonazepam, diazepam, estazolam, flunitrazepam, lorazepam, midazolam, nitrazepam, oxazepam, triazolam, temazepam, chlordiazepoxide, and alprazolam; herbal sedatives such as ashwagandha, *duboisia hopwoodii*, prosanthera striatiflora, kava (*piper methysticum*), mandrake, valerian, and marijuana; non-benzodiazepine sedatives (a.k.a. "Z-drugs") such as eszopiclone, zaleplon, zolpidem, zopiclone; antihistamines such as diphenhydramine, dimenhydrinate, doxylamine, and promethazine; and other sedatives such as chloral hydrate. Examples of anticholinergic agents include, without limitation, dicyclomine, atropine, ipratropium bromide, oxitropium bromide, and tiotropium. Examples of Parkinson's disease drugs include, without limitation, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, and lisuride. Examples of expensive agents include, without limitation, human growth hormone and erythropoietin. Examples of neuroleptic agents includes, without limitation, antipsychotics; butyrophenones such as haloperidol and droperidol; phenothiazines such as chlorpromazine, fluphenazine, perphenazine, prochlorperazine, thioridazine, trifluoperazine, mesoridazine, periciazine, promazine, triflupromazine, levomepromazine, promethazine, and pimozide; thioxanthenes such as chlorprothixene, clopenthixol, flupenthixol, thiothixene, and zuclopenthixol; atypical antipsychotics such as clozapine, olanzapine, risperidone, quetiapine, ziprasidone, amisulpride, asenapine, paliperidone, iloperidone, zotepine, and sertindole; and third generation antipsychotics such as aripiprazole and bifeprunox. Examples of TNF blockers includes, without limitation, etanercept.

In some embodiments, the hazardous agent can be selected from botulinum toxin, injectable gold, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, dexamethasone, progesterone, somatostatin, analogues of dexamethasone, analogues of progesterone, analogues of somatostatin, teriparatide, scopolamine, antihypertensives, blood pressure down regulators, fentanyl, fentanyl citrate, morphine, meperidine, other opioids, adalimumab (anti-tissue necrosis factor monoclonal antibody or anti-TNF), anakinra, daclizumab, basiliximab, azathioprine, cyclosporine, tacrolimus, testosterone, estrogen, growth hormone, insulin, thyroid hormone, follicle stimulating hormone (FSH), epinephrine/adrenaline, gamma-linolenic acid, docosahexanoic acid, arachidonic acid, eicosapentaenoic acid, amobarbital, pentobarbital, secobarbital, phenobarbitol, clonazepam, diazepam, estazolam, flunitrazepam, lorazepam, midazolam, nitrazepam, oxazepam, triazolam, temazepam, chlordiazepoxide, alprazolam, ashwagandha, duboisia *hopwoodii*, prosanthera striatiflora, kava (*piper methysticum*), mandrake, valerian, marijuana, eszopiclone, zaleplon, zolpidem, zopiclone, diphenhydramine, dimenhydrinate, doxylamine, promethazine, chloral hydrate, dicyclomine, atropine, ipratropium bromide, oxitropium bromide, tiotropium, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, lisuride, human growth hormone, erythropoietin, haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, etanercept, derivatives of any of the foregoing, and combinations of any of the foregoing.

While injection device 100 can deliver an injection of up to about 3 mL per injection, other volumes can be injected in alternative embodiments. In certain embodiments, injection device 100 can deliver an injection of greater than 1 mL per injection. In other embodiments, injection device 100 can deliver an injection in range of about 0.2 mL to about 3 mL.

In one embodiment, injector device 100 can inject 0.5 ml of a medicament dissolved in an aqueous solution in about 0.1 sec., about 0.2 sec., about 0.3 sec., about 0.4 sec., about 0.5 sec., about 0.6 sec., about 0.7 sec., about 0.8 sec., about 0.9 sec., about 1.0 sec., or any range determinable from the preceding times (for example, about 0.5 sec. to about 1.0 sec. or about 0.4 sec. to about 0.6 sec.). In another embodiment, injector device 100 can inject 0.5 ml of a medicament dissolved in oil in about 5 sec., about 6 sec., about 7 sec., about 8 sec., about 9 sec., about 10 sec., about 11 sec., about 12 sec., about 13 sec., about 14 sec., about 15 sec., or any range determinable from the preceding times (for example, about 6 sec. to about 7 sec. or about 5 sec. to about 15 sec.). In an alternate embodiment, injection device 100 can injection viscous materials in and about the ejection times as shown in Tables 1 and 2. Other volumes and times are determinable from the described preceding information and Tables 1 and 2.

Tables 1 and 2 show observed injection time for viscous oil medicament for one embodiment of injection device 100.

TABLE 1

Injection time - 27 g regular wall needle

| Volume | Time | Temperature |
|---|---|---|
| 0.2 ml | 6.9 sec | 10 C. |
| | 8.4 sec | |
| | 2.9 sec | 25 C. |
| | 3.3 sec | |
| 0.5 ml | 17.4 sec | 10 C. |
| | 21.1 sec | |
| | 7.4 sec | 25 C. |
| | 8.3 sec | |
| 1.0 ml | 34.7 sec | 10 C. |
| | 42.1 sec | |
| | 14.7 sec | 25 C. |
| | 16.6 sec | |
| 2.0 ml | 69.5 sec | 10 C. |
| | 84.2 sec | |
| | 29.5 sec | 25 C. |
| | 33.3 sec | |
| 3.0 ml | 104.2 sec | 10 C. |
| | 126.3 sec | |
| | 44.2 sec | 25 C. |
| | 49.9 sec | |

TABLE 2

Injection time - 27 g thin walled needle

| Volume | Time | Temperature |
|---|---|---|
| 0.2 ml | 2.8 sec | 10 C. |
| | 2.9 sec | |
| | 1.3 sec | 25 C. |
| | 1.5 sec | |
| 0.5 ml | 6.9 sec | 10 C. |
| | 7.3 sec | |
| | 3.3 sec | 25 C. |
| | 3.7 sec | |
| 1.0 ml | 13.9 sec | 10 C. |
| | 14.7 sec | |
| | 6.5 sec | 25 C. |
| | 7.3 sec | |
| 2.0 ml | 27.8 sec | 10 C. |
| | 29.4 sec | |
| | 13.1 sec | 25 C. |
| | 14.7 sec | |
| 3.0 ml | 41.6 sec | 10 C. |
| | 44.1 sec | |
| | 19.6 sec | 25 C. |
| | 22.0 sec | |

According to certain exemplary embodiments, injection device 100 can be configured to inject medicament stored within a prefilled syringe. Prefilled syringes that are manufactured by a blown glass process can have significant dimensional tolerances and unevenness. Accordingly, features of injection device 100 can serve to accommodate the shape irregularities and to properly position and locate a prefilled syringe within injection device 100. Other medicament containers such as prefilled syringes manufactured with polymers can also be accommodated. Further, in one embodiment, injection device 100 can be configured as a needle-assisted jet injector, providing a peak pressure during the injection of less than about 1,000 p.s.i., in one embodiment, less than 500 p.s.i., and in another embodiment less than about 400 p.s.i. In one embodiment, injection device 100 can provide a peak pressure during the injection of about 300 p.s.i., about 325 p.s.i., about 350 p.s.i., about 375 p.s.i., about 400 p.s.i., about 425 p.s.i., about 450 p.s.i., about 475 p.s.i., about 500 p.s.i., about 525 p.s.i., about 550 p.s.i., about 575 p.s.i., about 600 p.s.i., about 625 p.s.i., about 650 p.s.i., about 675 p.s.i., about 700 p.s.i., about 725 p.s.i., about 750 p.s.i., about 775 p.s.i., about 800 p.s.i., about 825 p.s.i., about 850 p.s.i., about 875 p.s.i., about 900 p.s.i., about 925 p.s.i., about 950 p.s.i., about 975 p.s.i., about 1,000 p.s.i., about 1,025 p.s.i., or any range determinable from the peak pressures (for example, about 500 p.s.i. to about 650 p.s.i. or about 1000 p.s.i. to about 1025 p.s.i.). At an end of an injection, the pressure applied to the medicament is, in one embodiment, at least about 80 p.s.i., in another embodiment, at least about 90 p.s.i., and, in another embodiment, at least about 100 p.s.i. In one embodiment, the pressure applied to the medicament at an end of an injection is about 50 p.s.i., about 60 p.s.i., about 70 p.s.i., about 80 p.s.i., about 90 p.s.i., about 100 p.s.i., about 110 p.s.i., about 120 p.s.i., about 130 p.s.i., or any range determinable from the pressures (for example, about 50 p.s.i. to about 60 p.s.i. or about 100 p.s.i. to about 110 p.s.i.). In one embodiment, the initial pressure can be around 330 p.s.i., and the final pressure can be about 180 p.s.i., while in another embodiment the initial pressure can be about 400 p.s.i., dropping to around 300 p.s.i. at the end of the injection. These exemplary pressures can, for example, result in a flow rate of about 0.2 mL/sec to 1.20 mL/sec, and, in one embodiment, be about 1.0 mL/sec. In one embodiment, the rate is greater than 0.2 mL/sec. In one embodiment, the injection device 100 may include an energy source 120, e.g., a high force spring, such as those needed for rapid ejection of difficult to eject medicaments. In one embodiment, energy source 120 is a high force spring of about 18 lbs. load capacity, about 18.5 lbs load capacity, about 19 lbs. load capacity, about 19.5 lbs. load capacity, about 20 lbs. load capacity, about 20.5 lbs. load capacity, about 21 lbs. load capacity, about 21.5 lbs. load capacity, about 22 lbs. load capacity, about 22.5 lbs. load capacity, about 23 lbs. load capacity, or any range determinable from the preceding load capacities (for example, about 18 lbs. load capacity to about 23 lbs load capacity or about 18 lbs. load capacity to about 19 lbs. load capacity). High force springs may be desired in situations where rapid delivery of drugs is important to assure injection of the entire dose; this would be to counteract users removing the injector from the injection site prematurely. Medicaments can be difficult to eject due to either high viscosity or because of a combination of their viscosity and a therapeutic need for delivery of the medicament using fine bore needles, such as the 29 gauge prefilled syringe. These exemplary high spring forces for difficult to inject medicaments can result in a flow rate of about 0.03 mL/sec to about 1.0 mL/sec.

In one embodiment, the needles used may be between 22 and 29 gauge. In some embodiments, the needles used are between 25 and 28 gauge, and, in other embodiments, are around 27 gauge, but alternatively other needle gauges can be used where the other components are cooperatively configured to produce the desired injection. In some embodiments, thin walled needles maybe used without risk of bending when injection device 100 is configured to act with manual needle insertion prior to injection. In certain jet injector embodiments firing aqueous medicaments, the firing mechanism, medicament container, needle, and energy source are configured to produce an average stream velocity within the needle of at least about 1,000 cm/sec, and, in certain embodiments, are at least about 1,300 cm/sec, up to about 3,000 cm/sec, and, in other embodiments, are up to about 8,000 cm/sec. In one embodiment, the average stream velocity during injection is about or reaches between about 1,300 and about 3,000 cm/sec or approximately about 2,000 cm/sec. In one embodiment, the average stream velocity during injection is about or reaches about 500 cm/sec, about 1,000 cm/sec, about 1,500 cm/sec, about 2,000 cm/sec, about 2,500 cm/sec, about 3,000 cm/sec, about 3,500 cm/sec, about 4,000 cm/sec, about 4,500 cm/sec, about 5,000 cm/sec, about 5,500 cm/sec, about 6,000 cm/sec, about 6,500 cm/sec, about 7,000 cm/sec, about 7,500 cm/sec, about 8,000 cm/sec, or any range determinable from the average stream velocities (for example, about 1,000 cm/sec to about 1,500 cm/sec or about 1,500 cm/sec to about 2,000 cm/sec). In one embodiment, the average stream velocity during injection is greater than about 750 cm/sec. In one embodiment, the average stream velocity during injection is greater than about 1250 cm/sec. In one embodiment, the average stream velocity during injection is less than about 5,000 cm/sec. In one embodiment, the average stream velocity during injection is less than about 3,000 cm/sec. In one embodiment, the average stream velocity during injection is less than about 2,000 cm/sec. The velocities used to produce a jet injection will vary for other types of medicaments, such as based on their viscosities. With some viscous medicaments, exemplary high spring forces can be used to produce stream velocity of about 100 cm/sec, up to about 1000 cm/sec. Weaker energy sources, and/or larger needles, for example, can be used to obtain lower velocities and lower pressures and/or flow rates for traditional, low-pressure autoinjector embodiments. Such embodiments can also benefit from the axial rotation between the trigger engagement member and the retaining portion, while moving from the pre-firing condition to the firing condition upon a proximal movement of the skin-contacting member with respect to housing. An example of which, but not limited to, is a reduction of friction between spring loaded components which can be applied to triggering designs not involving rotational motion.

In one embodiment, as shown in FIG. 1, the exemplary injection device 100 can include an outer housing 102 and a housing end/end cap 104. As shown in FIG. 1, in one embodiment, the housing end/end cap 104 is coupled to a proximal end of housing 102. Injection device 100 can further include various components and/or assemblies housed within outer housing 102. As shown in FIG. 1, these components can include a guard 106, a container support, such as, e.g., a sleeve 116, a firing mechanism 108, a medicament chamber 110, a needle 112, and a spring 114. As shown in FIG. 1, outer housing 102 can be a single piece component, or alternatively, outer housing 102 multiple piece assembly that can be coupled together, for example, via a snap-fit connection, a press-fit connection, a threaded engagement, adhesives, welding, or the like.

Figure 7B:
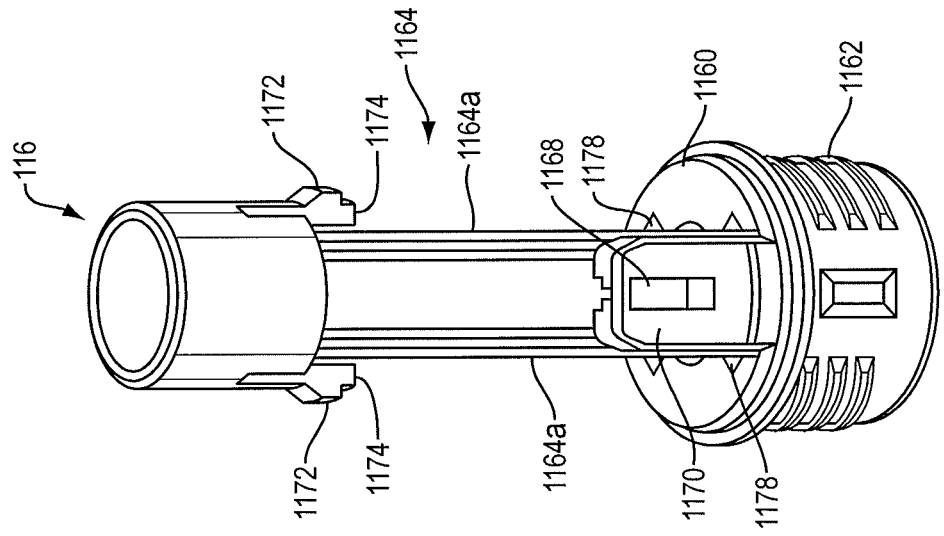
FIGS. 7A and 7B are side and perspective views of a sleeve of an exemplary injection device according to an exemplary embodiment of the present disclosure.
Figure 7A:
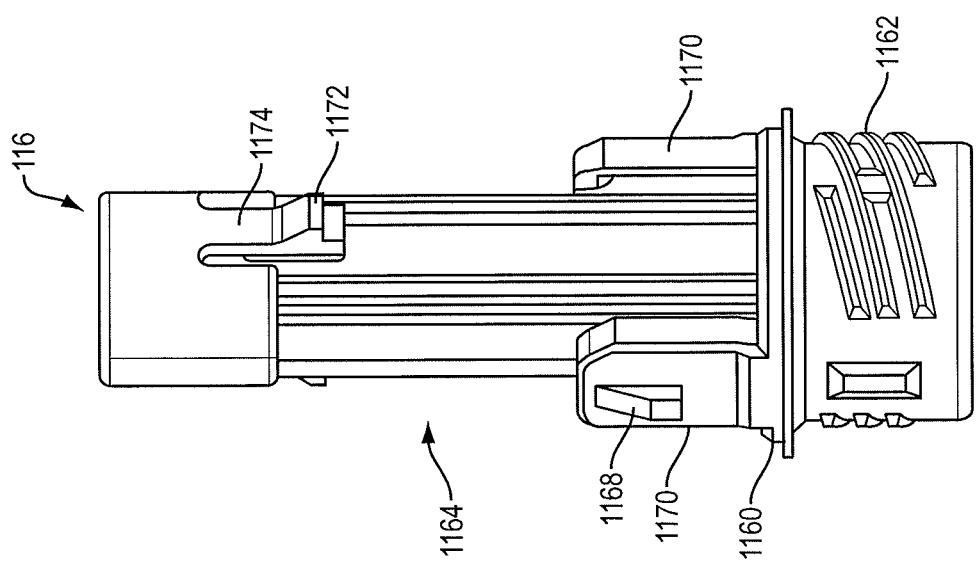

As shown in FIG. 1, in one embodiment, sleeve 116 is at least partially housed within outer housing 102 and mounted to outer housing 102 via, for example, a snap-fit connection, a press-fit connection, a threaded engagement, adhesives, welding, or the like. As shown in FIGS. 7A and 7B, for example, sleeve 116 can include projections 1168 configured to engage openings of housing 102. Sleeve 116 is configured to hold a medicament chamber 110, which can include a needle 112 at a distal end of medicament chamber 110. In certain exemplary embodiments, medicament chamber 110 can include, for example, a separate glass ampule and a needle, or a pre-filled syringe, or sleeve 116 itself can include an integral medicament chamber. In one embodiment, a plunger 118 is provided in the medicament chamber 110. Plunger 118 is in association with a ram 1232 of firing mechanism 108. During an injection, ram assembly 122 is urged by energy source 120 of firing mechanism 108 to displace plunger 118 distal, deeper into medicament chamber 110, dispensing the medicament through needle 112. In one embodiment, needle 112 includes an injecting tip 112a that is configured to penetrate the skin of a user and a hollow bore 112b that is in fluid communication with medicament chamber 110 to facilitate delivery of medicament from medicament chamber 110 to a user during an injection. FIG. 1 shows injection device 100 in a pre-firing state. The operation of injection device 100, including its various stages and positions, are described in further detail below.

As also shown in FIG. 1, injection device 100 also, in certain embodiments, includes firing mechanism 108. In one embodiment, firing mechanism 108 includes a ram assembly 122 slidably mounted within housing 102 and an energy source 120. In an exemplary embodiment, the energy source 120 includes a compression spring 120, however, other suitable energy source can be used, such as an elastomer or compressed-gas spring, or a gas generator, or other suitable energy storage members. In FIG. 1, ram assembly 122 is in a pre-firing proximal-most position. During an injection, ram assembly 122 is urged distally by energy released by energy source 120. Once an injection is completed, firing ram assembly 122 is disposed in a distal-most position. In this distal position, guard 106 is locked-out and extends over needle tip so that a user cannot attempt a subsequent injection and the needle guard 106 can function as sharps protection. Although shown as a single piece, ram assembly 122 can be a multiple piece assembly that can be coupled together, for example, via a snap-fit connection, a press-fit connection, a threaded engagement, adhesives, welding, or other suitable couplings. Ram assembly 122 preferable includes various features that can be configured to facilitate firing of injection device 100 to dispense the medicament stored in medicament chamber 110. According to certain exemplary embodiments of the present disclosure, a trigger mechanism of injection device 100 can include ram assembly 122, the floating trigger member 300, which can include a retaining portion 302, and ram retaining holding member 1042.

Figure 2:
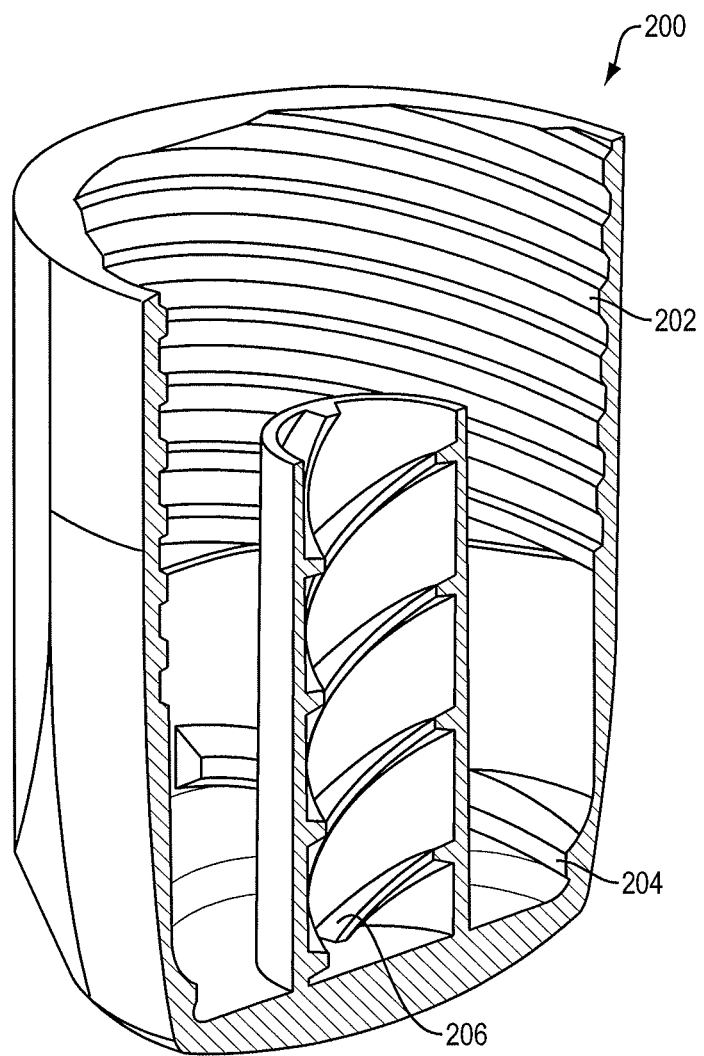
FIG. 2 shows a cross sectional view of a cap of an exemplary injection device according to an exemplary embodiment of the present disclosure.

In one embodiment, injection device 100 includes a cap 200, as shown in FIG. 2. The cap 200 may be removably affixable to a distal end of outer housing 102. In one embodiment, the cap 200 may be removably affixable to the distal end of sleeve 116. For example, cap 200 can be removably affixed to the distal end of housing 102 via a threaded engagement and housing end/end cap 104 can include features (e.g., projections) configured to engage a portion of the proximal end of housing 102 (e.g., openings) to couple housing end/end cap 104 to housing 102. When affixed to injection device 100, the cap 200 can ensure that an injection is not triggered by an inadvertent application of a force to guard 106. In one embodiment, the cap 200 includes two engagement features. As shown in FIG. 2, the cap 200 can include engagement features 202 and 204. Engagement features 202 and 204 can be threads configured to threadedly engage other features of injection device 100. For example, engagement feature 202 can be configured to secure cap 200 to the distal end of housing 102 or be configured to threadedly engage a distal portion of sleeve 116. In one embodiment, engagement feature 204 can be configured to threadedly engage features (e.g., threads) of guard 106 to prevent proximal displacement of guard 106.

As shown in FIG. 2, cap 200 has any regular or irregular shape and may be non-circular in cross-section viewed along its axis and in the initial, closed position aligns with or substantially matches the shape of the portion of the housing adjacent thereto. In one embodiment, features 202 and 204 may include a plurality of threads, having more than one thread starting point, only one of which will result in the cap lining up with the housing as in the initial closed position. Consequently, if the cap is removed and replaced, there is a chance that an incorrect starting point will be selected by the user, resulting in the cap no longer aligning with the injector housing, and providing an indication of tampering. In one embodiment, three threads are used, so there is a two in three chance that a removed and replaced cap will become immediately obvious based on an ill-fitting cap.

As shown in FIG. 1, in one embodiment, housing 102 includes openings configured to engage with sleeve 116 to couple and secure sleeve 116 to housing 102 and includes at least one window that can provide a visual indication of whether or not injection device 100 has been fired. For example, in an pre-firing state, the window allows a user to see medicament chamber 110, along with the stored medicament, and in a fired state, the window shows one or more internal components, such as a portion of firing mechanism 108, which can be a color specifically selected to alert the user that injection device 100 has been fired, and is, in one embodiment, sufficiently different than other colors visible to a user (in one embodiment, having ordinary eyesight) on the injector prior to firing, so as to be conspicuously different to, or contrast from, any other colors present or significantly present. For example, in one embodiment, the color differs from all the other components of injection device 100 pre-firing, or visible by the user pre-firing, so as to be conspicuous (e.g., introducing an entirely new color family). In one embodiment, the new color appearing after firing, is from a non-analogous part of the color wheel, or can contrast, or can be a complementary color, with respect to the colors visible on injection device 100. In one embodiment, the new color signifies caution, such as red or orange, etc. In one embodiment, the colors visible on the injector in the pre-firing condition, and, in one embodiment, including when the cap 200 is on and/or off the injector, are grays and blues, for instance. In one embodiment, when the injector is fired, the color red is introduced. In one embodiment, this new color can be introduced after firing but prior to guard 106 being locked-out in the extended position.

Figure 3A:
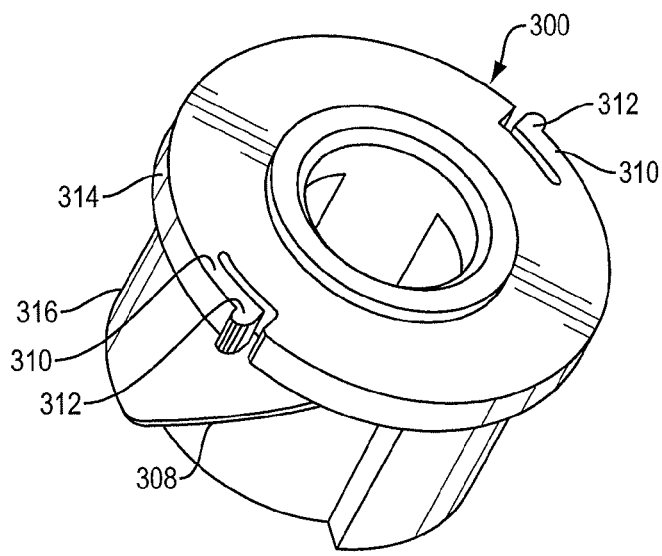
FIG. 3A is a perspective view of a floating trigger member of an exemplary injection device according to an exemplary embodiment of the present disclosure.
Figure 3B:
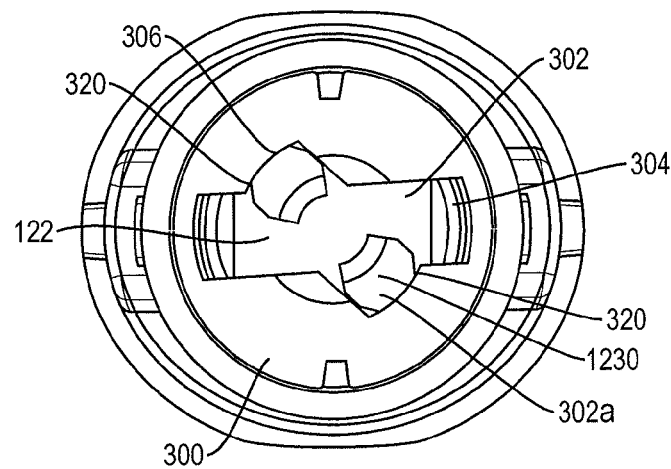
FIG. 3B is a cross-section view at section break 3B,3C of an exemplary injection device according to an exemplary embodiment of the present disclosure in a ram retaining position.
Figure 3C:
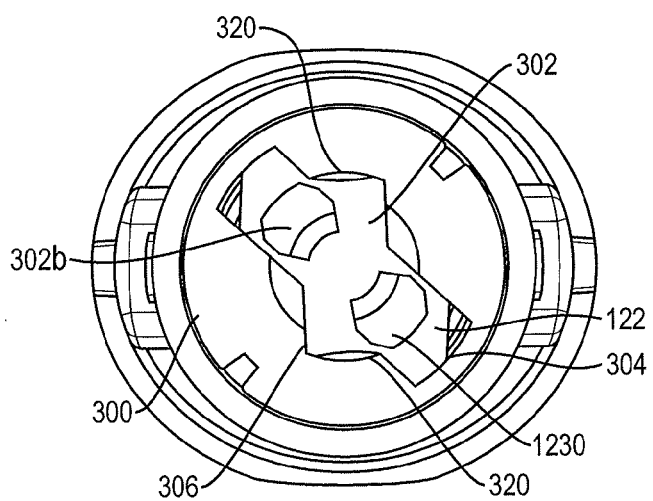
FIG. 3C is a cross-section view at section break 3B,3C of an exemplary injection device according to an exemplary embodiment of the present disclosure in a firing position.

In one embodiment, the injection device 100 includes a floating trigger member 300, as shown in FIGS. 3A, 3B and 3C. The floating trigger member 300 can have a proximal portion 314 and a distal portion 316. In one embodiment, the floating trigger member 300 can include an opening 302. Further, the floating trigger member 300 can include an opening 302 in the distal portion 316. The opening 302 can include a retaining portion 306 configured to receive and engage trigger engagement member 1230 of ram assembly 122 in facilitating firing of injection device 100. The opening 302 is, in one embodiment, configured to engage a trigger engagement member 1230 of ram assembly 122 such that they are aligned in one of two positions. For example, in first position 302a (e.g., retaining position), trigger engagement members 1230 of ram assembly 122 are aligned so that they can be restrained by the retaining portion 306, thereby preventing firing mechanism 108 from firing and dispensing the medicament. In second position 302b (e.g., firing position), the opening 302 can include firing portions 304 such that the trigger engagement members 1230 of ram assembly 122 are aligned such that trigger engagement members 1230 can splay apart, thereby permitting firing mechanism 108 to fire. FIG. 3B shows trigger engagement members 1230 aligned in the first position (302a) and FIG. 3C shows trigger engagement members 1230 aligned in the second position (302b). Further, the retaining portion 306 of the opening 302 (e.g., in the first position 302a) is, in one embodiment, curved to facilitate rotation of the floating trigger member 300 from the first and second positions. An exterior surface of distal portion 316 of the floating trigger member 300 can include camming surfaces 308. In one embodiment, a portion of trigger engagement members 1230 optionally engage rests 320, such that when floating trigger member 300 rotates, trigger engagement members 1230 disengage rests 320 allowing firing mechanism 108 to fire.

Figure 6A:
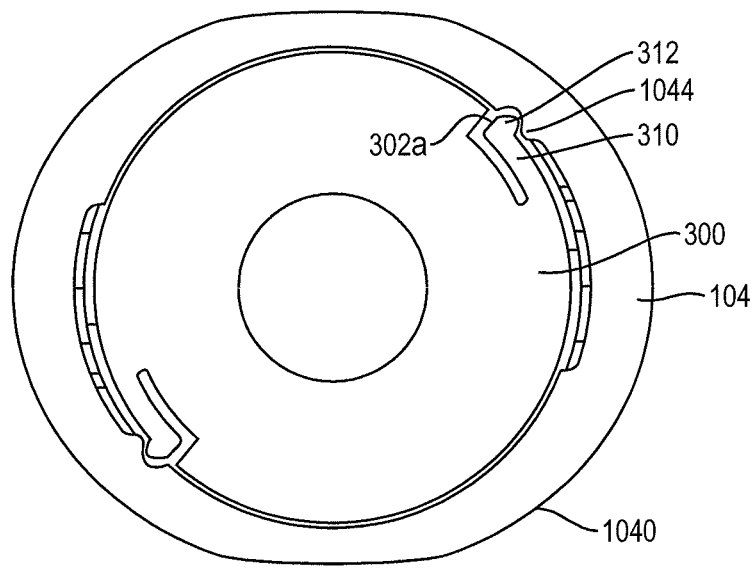
FIG. 6A is a cross-section view at section break 6B,6C of an end housing portion and floating trigger member of an exemplary injection device according to an exemplary embodiment of the present disclosure in a retaining position.
Figure 6B:
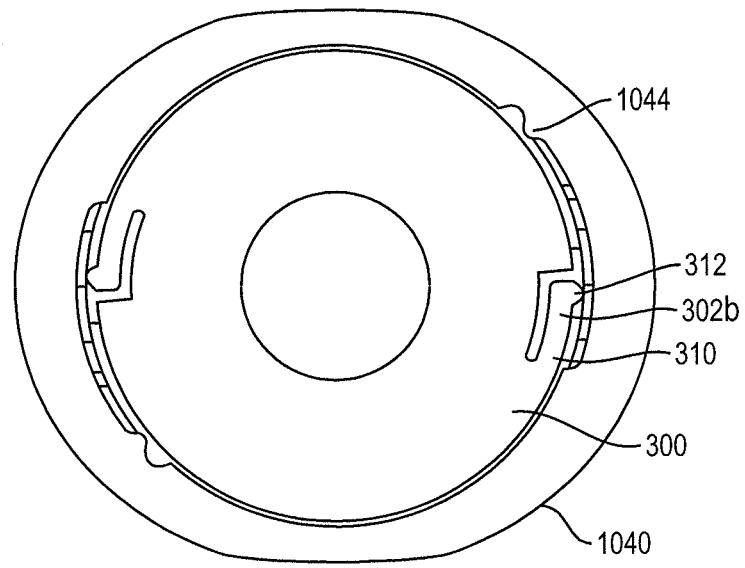
FIG. 6B is a cross-section view at section break 6B,6C of an end housing portion and floating trigger member of an exemplary injection device according to an exemplary embodiment of the present disclosure in a firing position.

The proximal portion 314 of the floating trigger member can include flanges 310 having lips 312, described further below with reference to FIG. 6.

In one embodiment, as shown in FIG. 1, energy source 120 (e.g., a spring) is decoupled from guard 106. In one embodiment, the proximal end energy source 120 is coupled to housing 102. By decoupling energy source 120 from guard 106, the apparent friction of rotation of floating trigger member 300 is significantly reduced. This in turn substantially reduces the amount of force necessary to move guard 106 from an extended position to the firing position as described with reference to FIGS. 9A and 9B, below. Specifically, the compression of components caused by energy source 120 is substantially eliminated thereby significantly reducing the amount of apparent friction and resistance to movement of guard 106 during use of injection device 100.

Figure 4:
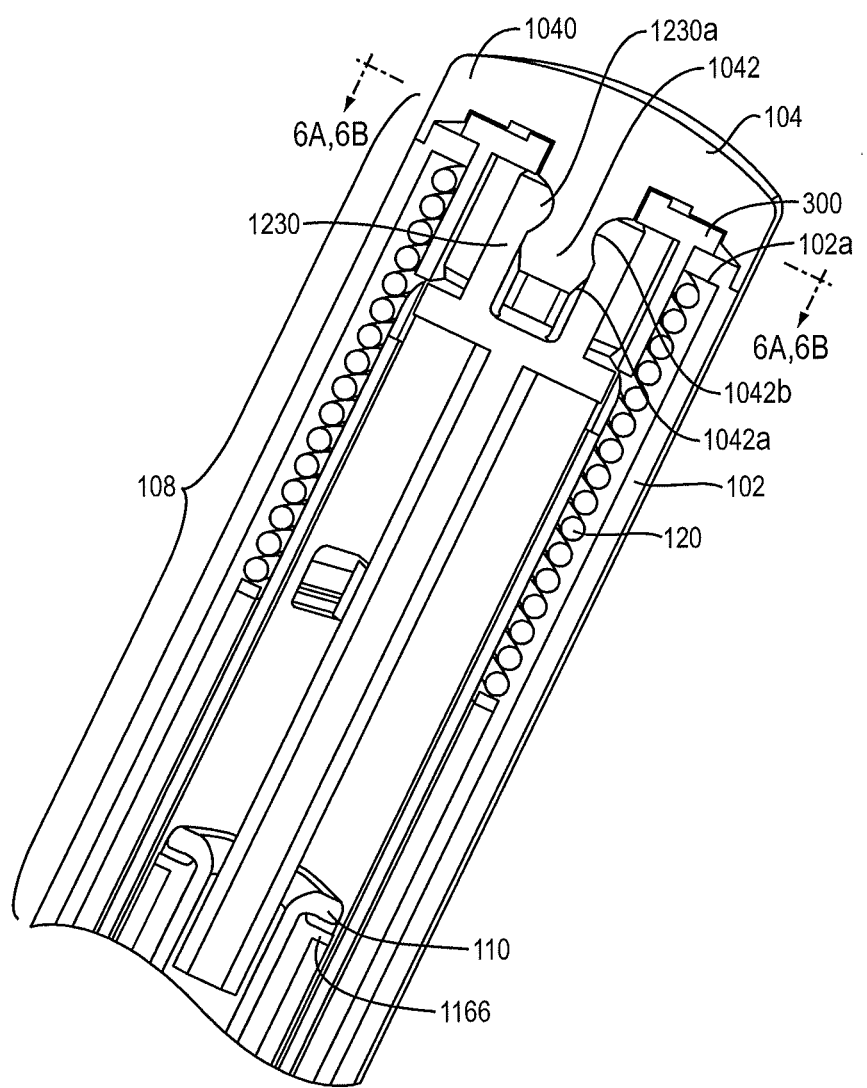
FIG. 4 is a partial cross-sectional view of an exemplary injection device according to an exemplary embodiment of the present disclosure.
Figure 5A:
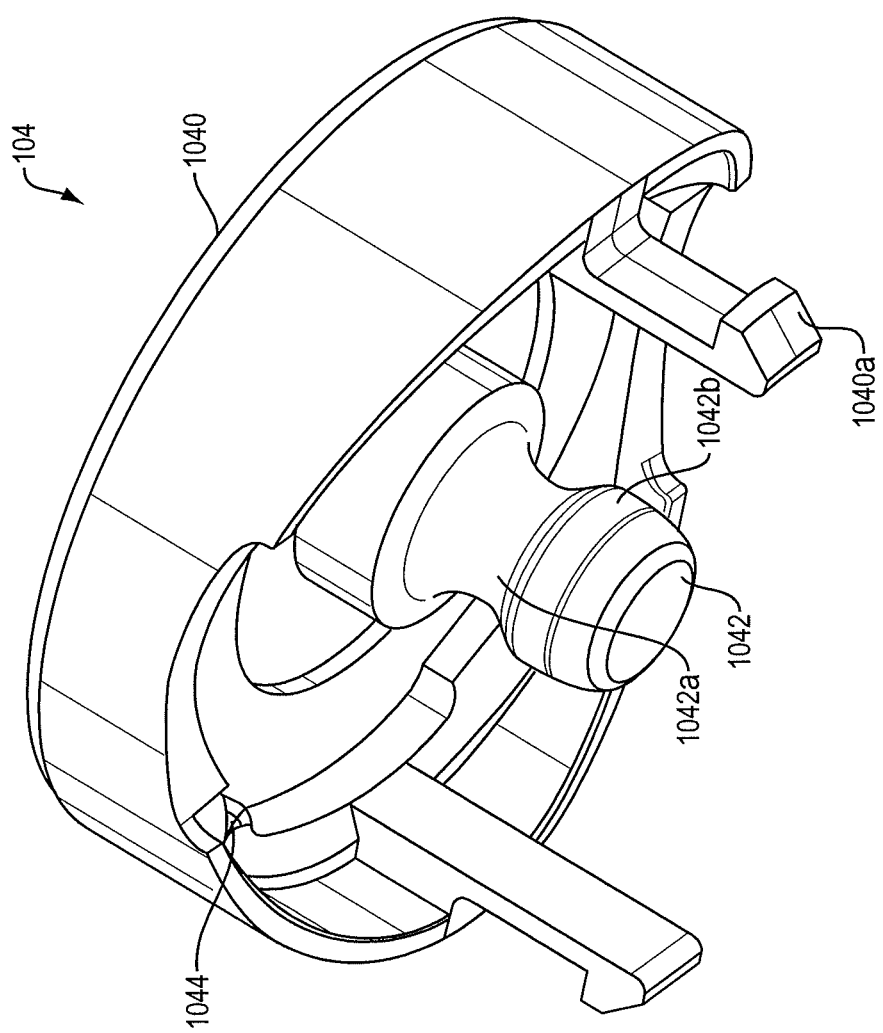
FIG. 5A is a perspective view of an end housing portion of an exemplary injection device according to an exemplary embodiment of the present disclosure.
Figure 5B:
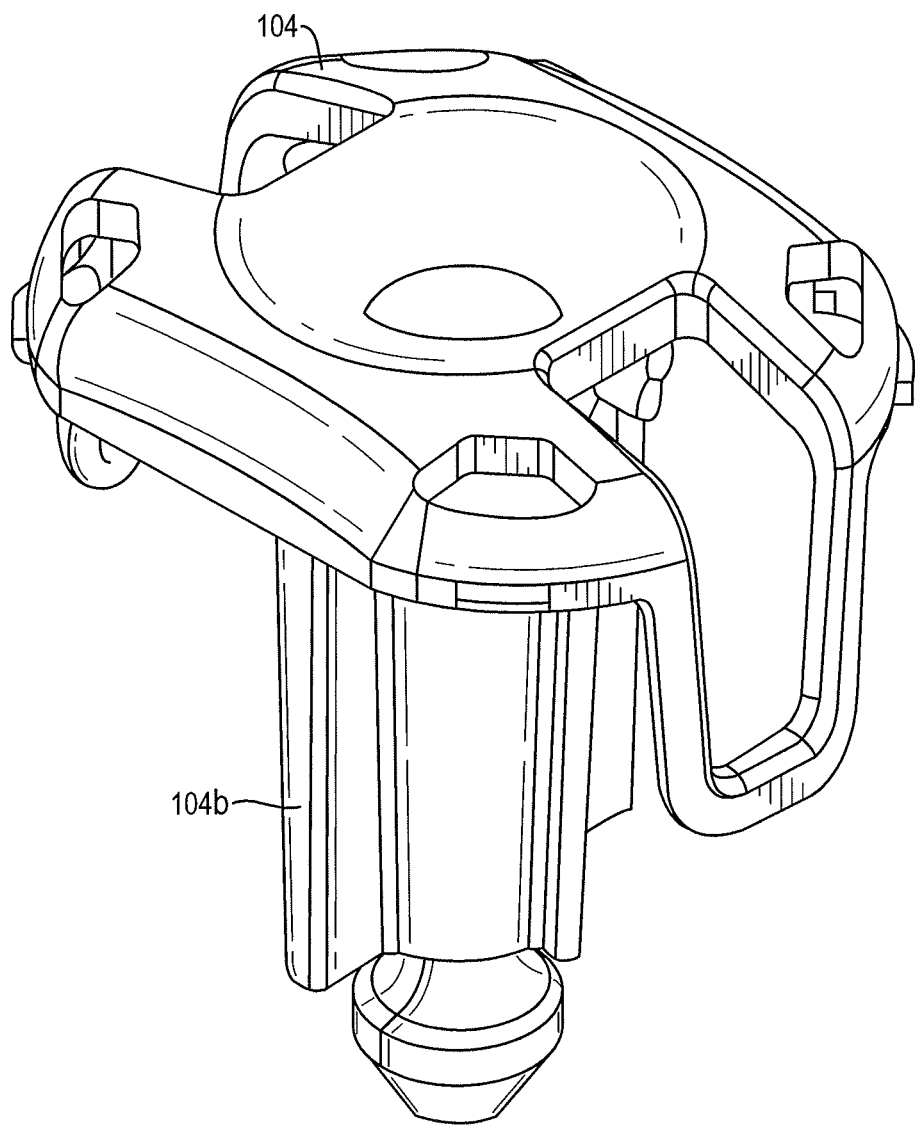
FIG. 5B is a perspective view of an end housing portion of an exemplary injection device according to an exemplary embodiment of the present disclosure.

As shown in FIG. 1, in one embodiment, injection device 100 also includes housing end/end cap 104. One embodiment of a housing end/end cap 104 is shown in FIG. 5A. As shown in FIG. 5A, in one embodiment, housing end/end cap 104 includes a body portion 1040 and a ram holding member 1042. In one embodiment, ram holding member 1042 is a projection, and is configured to engage a trigger engagement member of firing mechanism 108. For example, as shown in FIG. 4, in one embodiment, ram holding member 1042 is a bell-shaped projection, and is engaged with a complementary shaped feature (e.g., projections) 1230a of firing mechanism 108. As shown in FIG. 4, in an exemplary embodiment, ram holding member 1042 can include a groove 1042a and a bulge 1042b, and features 1230a of firing mechanism 108 can be configured to align with groove 1042a so as to hold bulge 1042b to prevent firing of injection device 100. In one embodiment, ram holding member 1042 and the features 1230a of firing mechanism 108 engaging with ram holding member 1042 include a circular cross section to allow rotation of the features of firing mechanism 108 relative to ram holding member 1042 during firing of injection device 100. As shown in FIG. 5A, further, body portion 1040 can include projections 1040a configured to engage openings in outer housing 102 to couple housing end/end cap 104 to housing 102. FIG. 5B shows another embodiment of a housing end/end cap 104.

In an exemplary embodiment, the housing end/end cap 104 optionally includes an engagement member 1044, as shown in FIG. 5A. As further detailed in FIGS. 6A and 6B, the engagement member 1044 engages lip 312 of the floating trigger member 300 when the floating trigger member 300 is rotated from the first position to the second position.

In certain embodiments having engagement member 1044 and lip 312, a threshold breakaway force is needed to overcome the resistance on the floating trigger member 300 caused by the engagement portion 1044 when the floating trigger member 300 is moved at least partially from the first position to the second position. In certain embodiments, the breakaway feature serves as a safety to prevent unintended rotation of the floating trigger member 300.

Figure 13:
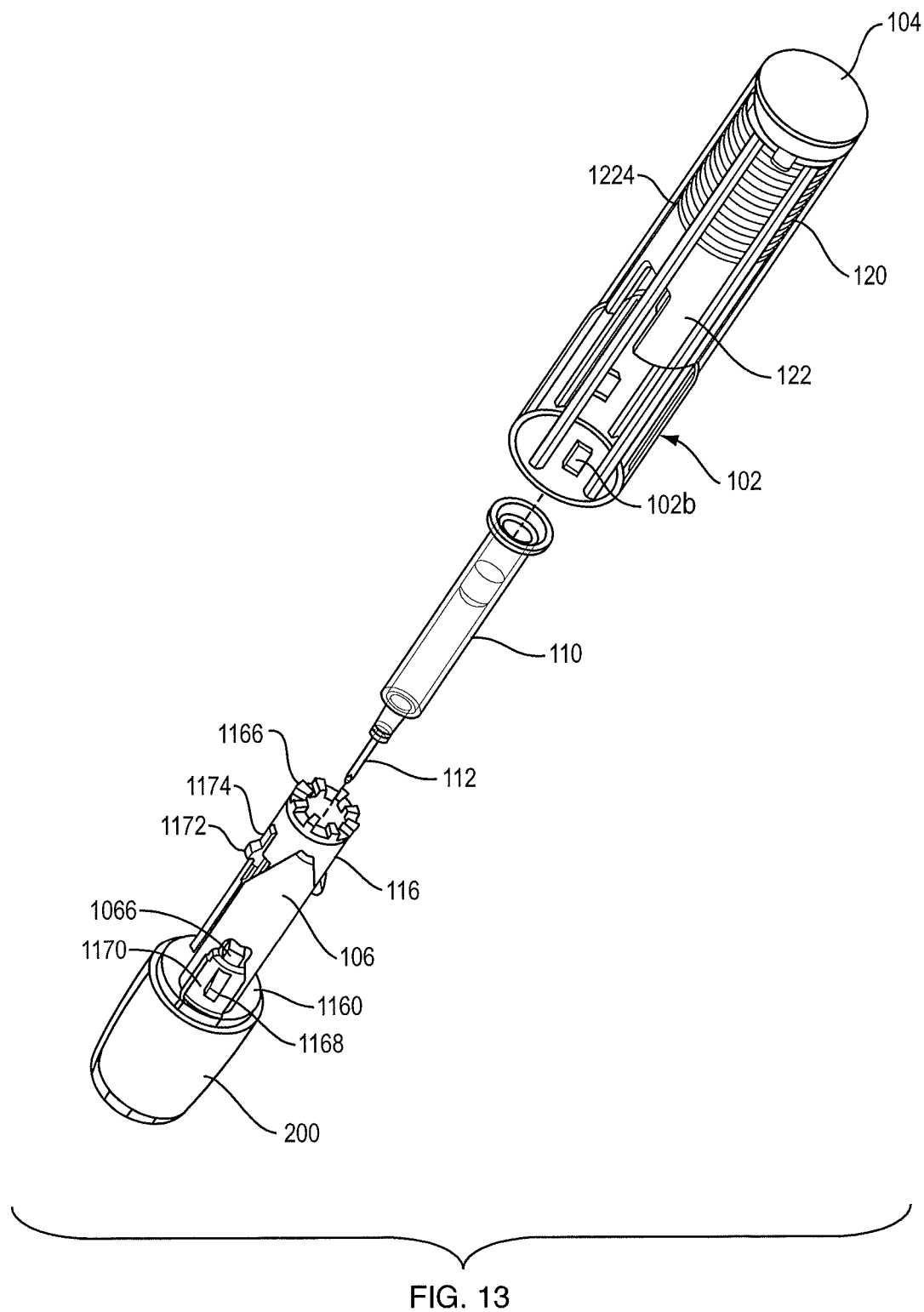
FIG. 13 is an exploded view of an exemplary injection device according to an exemplary embodiment of the present disclosure.

As shown in FIGS. 7A and 7B, in one embodiment, sleeve 116 includes a ring-like structure 1160, a coupling arrangement 1162, and a body portion 1164. Coupling arrangement 1162 can be disposed at a distal portion of sleeve 116 and can be configured to releasably engage cap 200. For example, as seen in FIGS. 1 and 2, coupling arrangement 1162 can include threads configured to provide threaded engagement between sleeve 116 and cap 200. Further, sleeve 116 can include a body portion 1164 configured to secure medicament chamber 110. Body portion 1164 can include guides, such as grooves 1164a, configured to engage with features of guard 106 to align and guide axial displacement of guard 106. As shown in FIG. 13, a proximal end of sleeve 116 can include a medicament chamber support 1166 configured to support and secure a proximal portion of medicament chamber 110. For example, support 1166 can be configured as a syringe support configured to hold a proximal end of syringe (e.g., flanges of a prefilled syringe) and can support medicament chamber 110 during the forces exerted on it during firing. Further, support 1166 can include an elastomer or a rubber, and can be configured to distribute the force exerted on surfaces of the medicament chamber 110 during an injection and protect the medicament container from shock during transport or inadvertent damage during use. Additionally, as shown in FIGS. 7A and 13, sleeve 116 can include various features, such as projections 1168, configured to couple sleeve 116 to outer housing 102. For example, projections 1168 can be concentrically symmetrical and configured to engage openings 102b in outer housing 102 to secure sleeve 116 to outer housing 102. In an exemplary embodiment, projections 1168 can be disposed on legs 1170, which can be concentrically symmetrical and configured to engage with features of the outer housing 102. Additionally, sleeve 116 can include locking features, such as locking projections 1172, disposed on legs 1174, which can be concentrically symmetrical, and can be configured to engage with features of guard 106 of firing mechanism 108 resulting in locking out injection device 100 to prevent a user from attempting to use an already-fired injection device 100.

In one embodiment, ring-like structure 1160 includes several features configured to engage sleeve 116 with medicament chamber 110 (e.g., a glass medicament chamber 110), firing mechanism 108, and guard 106. For example, ring-like structure 1160 can include an opening through which needle 112 can be received. Further, ring-like structure 1160 can include concentrically symmetrical openings 1178 which can be configured to receive legs of guard 106. Additionally, ring-like structure 1160 can be configured to support a distal portion of medicament chamber 110 and engage firing mechanism 108 in preventing further axial displacement of firing mechanism 108 during dispensing of the medicament. Operations of these components are described in further detail below.

Figure 9B:
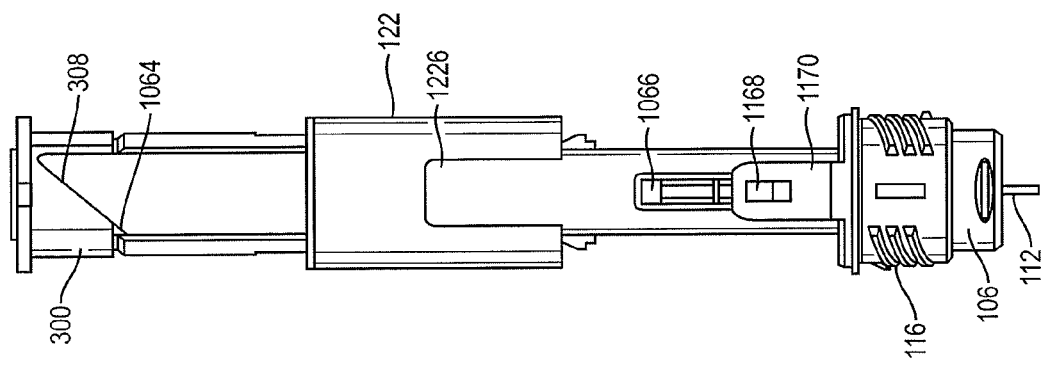
FIGS. 9A and 9B are side views of a ram assembly, needle guard, floating trigger member, sleeve an of an exemplary injection device according to an exemplary embodiment of the present disclosure in unfired and fired positions, respectively.
Figure 9A:
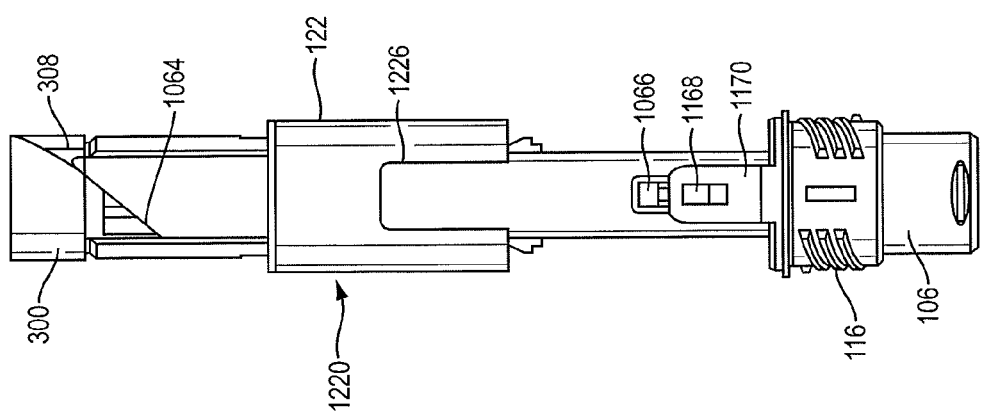

As shown in FIG. 1, in one embodiment, injection device 100 includes a guard 106 slidably mounted at least partially within outer housing 102 and configured to engage trigger member 300 to actuate firing of injection device 100. As shown in FIGS. 9A and 9B, in one embodiment, guard 106 is slidably movable relative to outer housing 102 between an extended (e.g., a distal, protective) position and a retracted (e.g., proximal) position, repsectively. In the extended position, guard 106, in one embodiment, covers needle 112, and in the retracted position, needle 112 is not covered by guard 106 and is thereby exposed. For example, FIG. 9A shows guard 106 in the extended position, and FIG. 9B shows guard 106 in the retracted position. As shown in FIG. 1, in one embodiment, guard 106 is resiliently biased toward the extended position via a spring 114, which can be disposed, for example, between a distal surface of ring-like structure 1160 of sleeve 116 and an interior surface of a distal end of guard 106.

In an exemplary embodiment, guard 106 includes a distal portion 1060 and legs 1062. In an exemplary embodiment, the distal end of guard 106 includes a skin-contacting member. Distal portion 1060 includes an opening through which needle 112 can pass and projections 1060a. In an exemplary embodiment, projections 1060a can be configured to engage engagement features 204 of cap 200 so that guard 106 cannot be proximally displaced when engaged with engagement features 204 of cap 200. In an exemplary embodiment, the guard 106 includes a stop surface 1070. In an exemplary embodiment, the stop surface 1070 can be configured to abut an inside surface of the ring like structure 1160 of sleeve 116 so as to limit the proximal displacement of guard 106. For example, as guard 106 is proximally displaced under a force applied by a user during an injection, stop surface 1070 will come into contact with the inside surface of the ring like structure 1160 of sleeve 116 so that guard 106 cannot be further proximally displaced.

Figure 8:
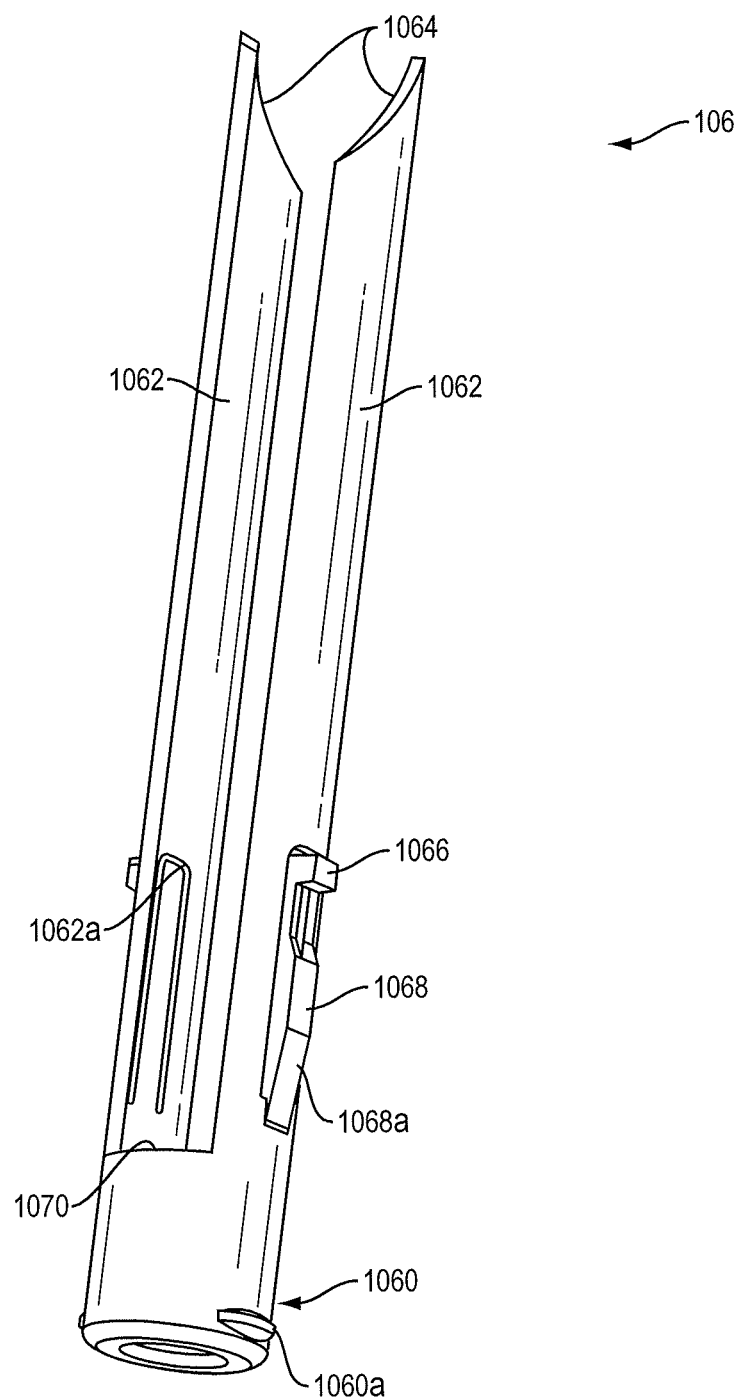
FIG. 8 is a side and perspective views of a needle guard of an exemplary injection device according to an exemplary embodiment of the present disclosure.

In one embodiment, legs 1062 of guard 106 are configured to be received in openings 1178 of ring-like structure 1160. Further, legs 1062 can include ridges 1062a configured to engage grooves 1164a of sleeve 116, to facilitate alignment and guiding of legs 1062 as guard 106 is axially displaced. As shown in the exemplary embodiment of FIG. 8, legs 1062 also include firing-initiation members, such as camming surfaces 1064 at a proximal end of legs 1062. In an exemplary embodiment, legs 1062 and camming surface 1064 can be concentrically symmetrical. Camming surfaces 1064 are configured to engage trigger member 300 in initiating a firing of injection device 100 and performing an injection of the medicament stored in medicament chamber 110. The proximal ends of legs 1062 can also be sloped to facilitate legs 1062 being received within firing mechanism 108 when guard 106 is displaced from the extended position to the retracted position. As shown in FIGS. 9A and 9B, in an exemplary embodiment, the camming surfaces 1064 are configured to engage camming surfaces 308 of the floating trigger member 300. In one embodiment, legs 1062 include projections 1066 disposed on springs 1068 which can also include sloped surfaces 1068a. As shown in FIG. 13, projections 1066 can be configured to engage proximal surfaces of legs 1170 of sleeve 116 to oppose a force exerted by spring 114, which biases guard 106 in the extended position. Further, sloped surfaces 1068a of legs 1062 of guard 106 can be configured to engage an interior surface of legs 1170 of sleeve 116 so that as guard 106 is displaced from the extended position to the retracted position, sloped surfaces 1068a of legs 1062 of guard 106 engage the interior surfaces of legs 1170 of sleeve 116 so as to bias springs 1068 of legs 1062 of guard 106 towards an interior of injection device 100.

FIG. 9A shows engagement of camming surfaces 1064 of the guard with camming surfaces 308 of the floating trigger member 300 in a pre-firing "ready-to-use" state. FIG. 9B shows engagement of camming surfaces 1064 of the guard with camming surfaces 308 of the floating trigger member 300 in a triggered or "just-fired" state. As guard 106 is moved in the proximal direction, the axial movement of guard 106 is translated into a rotational movement of the floating trigger member 300 via the engagement of camming surfaces 1064 and 308.

In an exemplary embodiment as shown in FIGS. 10A and 10B, ram assembly 122 containing ram 1232 can include a distal portion 1220 and a proximal portion 1222 separated by a feature 1224, such as a lip, a ledge, that can be configured to act as a seat for energy source 120. As shown in FIG. 13, in an exemplary embodiment, compression spring as the energy source 120 can be disposed between a proximal end of housing 102 and feature 1224. As shown in FIG. 4, in an exemplary embodiment, housing 102 includes a feature 102a, such as a lip, that is configured to act as a seat for energy source 120. Feature 102a can be designed or include elements that reduce friction due to compression spring rotation when energy source 120 is in contact with feature 102a in housing 102. Ram assembly 122 including distal portion 1220 can be substantially cylindrical and can be configured to concentrically receive at least a portion of sleeve 116 and guard 106. Distal portion 1220 can also include openings 1226 configured to receive legs 1170 of sleeve 116 and projection 1066 of guard 106.

In one embodiment, proximal portion 1222 includes legs 1228, a ram 1232, and a trigger engagement member 1230. Although the trigger engagement member 1230 is shown as projections, alternative implementations are contemplated. The trigger engagement member 1230 can include any feature (e.g., an elongated tab, a thinned tab, a recess, a protrusion, a bulge, a thread, etc.) that can be held by ram retaining member in the pre-firing state, and released upon rotation of the floating trigger member.

As shown in FIGS. 9A and 9B, in one embodiment, camming surface 1064 of guard 106 and camming surface 308 of floating trigger member 300 are oriented at an angle with respect to the longitudinal axis of the device to achieve a selected force and throw required to depress the guard 106 from the extended to the retracted position to fire the device. In some embodiments, the camming surfaces are angled at between 15° and 75° with respect to the axis, and, in one embodiment, between about 20° and 45°. In one embodiment, the camming surfaces are angles at about 30° with respect to the axis.

Figure 11:
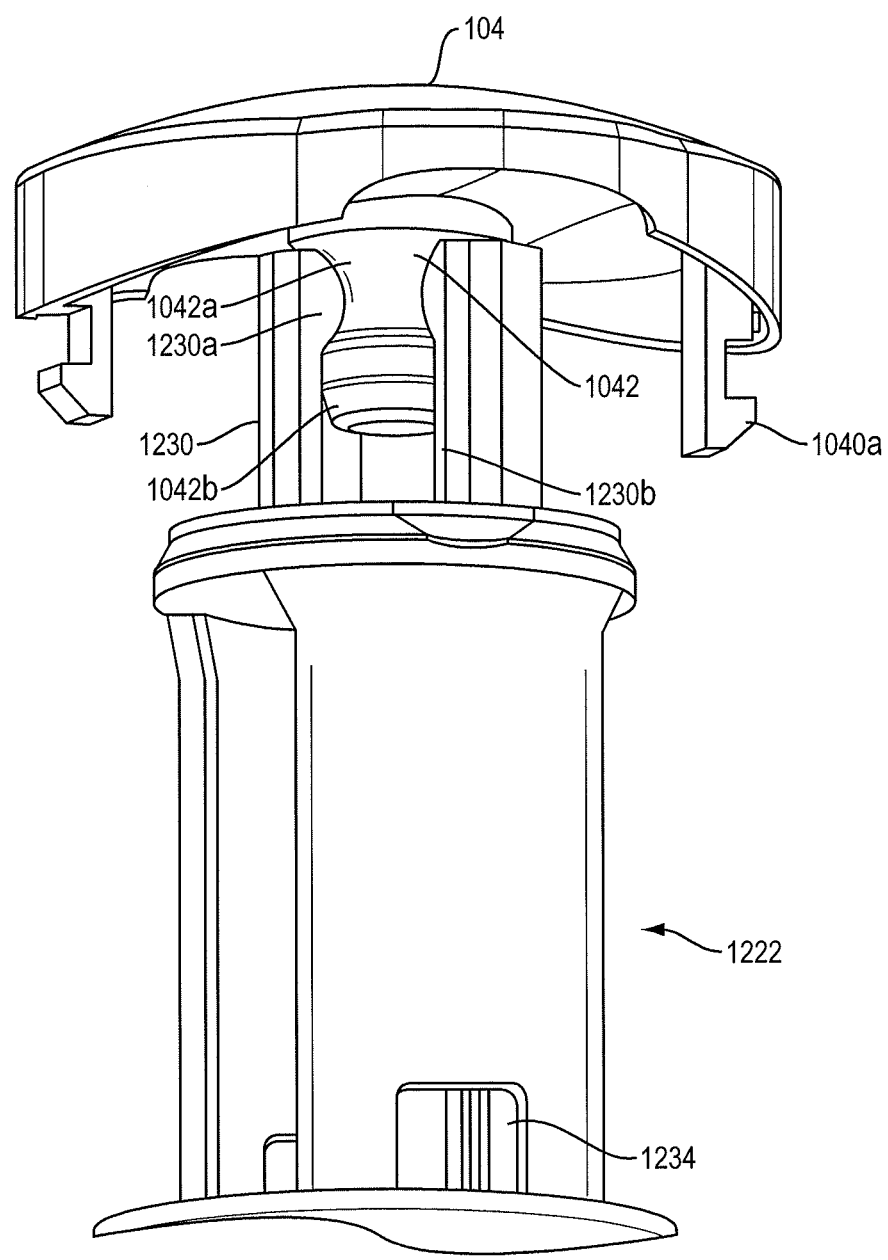
FIG. 11 shows a close-up view of an engagement of a trigger engagement member and a ram retaining member of an exemplary injection device according to an exemplary embodiment of the present disclosure.

As shown in FIGS. 10A and 10B, legs 1228 include openings 1234 configured to engage locking projections 1172 of sleeve 116. It is understood that openings 1234 accommodating alternate specific delivery volumes may be configured on distal portion 1220 to engage locking projections 1172 of sleeve 116. As shown in FIG. 10, for example, locking projections 1172 of sleeve 116 can engage openings 1234 of ram assembly 122 after injection device 100 has been fired, locking-out injection device 100 so that a user cannot initiate subsequent retraction of guard 106 exposing needle 112. Ram 1232 is configured to be in association with plunger 118, and distally displace plunger 118 under the force of energy source 120 to dispense the medicament contained in medicament chamber 110 during an injection. Additionally, trigger engagement members 1230 can be disposed at a proximal end of proximal portion 1222 and can be configured to engage opening 302 of floating trigger member 300 and ram holding member 1042 of housing end/end cap 104. The engagement of trigger engagement members 1230 with opening 302 and ram holding member 1042, as well as the alignment of trigger engagement members 1230 within opening 302 can control and enable firing of injection device 100. For example, trigger engagement members 1230 can include bulges 1230a configured to engage groove 1042a of ram holding member 1042, and shapes 1230b configured to engage bulge 1042b of ram holding member 1042. As noted above, trigger engagement members 1230 and ram holding member 1042 preferably include circular cross-sections to allow rotation of floating trigger member 300 during firing of injection device 100. FIG. 11 shows a close-up view of an embodiment of the engagement of trigger engagement member 1230 (e.g., projections) with one embodiment of ram holding member 1042.

In certain embodiments, as shown in FIGS. 17A, 17B, 17C, and 17D, the engagement of the bulges 1230a of trigger engagement members 1230 of ram assembly 122 with ram holding member 1042 of housing end/end cap 104 creates a latch retention angle 172. In one embodiment, latch retention angle 172 is defined by axis 170 and the contact surface of a distal portion of groove 1042a of ram holding member 1042 and bulges 1230a of ram assembly 122. In certain embodiments, projections 1230 and ram holding member 1042 are sized and shaped to create, when engaged, a latch retention angle 172 of about 10°, about 11°, about 12°, about 13°, about 14°, about 15°, about 16°, about 17°, about 18°, about 19°, about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, about 40°, about 41°, about 42°, about 43°, about 44°, about 45°, about 46°, about 47°, about 48°, about 49°, about 50°, about 51°, about 52°, about 53°, about 54°, about 55°, about 56°, about 57°, about 58°, about 59°, about 60°, about 61°, about 62°, about 63°, about 64°, about 65°, about 66°, about 67°, about 68°, about 69°, about 70°, about 71°, about 72°, about 73°, about 74°, about 75°, about 76°, about 77°, about 78°, about 79°, about 80°, about 81°, about 82°, about 83°, about 84°, about 85°, about 86°, about 87°, about 88°, about 89° or any range determinable from the preceding angles (for example, about 39° to about 41° or about 79° to about 81°).

In certain embodiments, in a pre-fired state, trigger engagement members 1230 are engaged with the wall of the opening of the trigger member (e.g., opening 302 of floating trigger member 300 or opening 1408 of trigger member 1400 (as discussed in more detail below)), bulges 1230a of ram assembly 122 and ram holding member 1042 of housing end/end cap 104 are engaged, and energy source 120 is acting on ram assembly 122. In one embodiment, the engagement of bulges 1230a and ram holding member 1042 hold ram assembly 122 in place against the distally-directed force being applied to ram assembly 122 by energy source 120. In one embodiment, in a pre-fired state, energy source 120 is applying axial force on ram assembly 122, which causes bulges 1230a of projections 1230 of ram assembly 122 to engage bulge 1042b of ram holding member 1042. In one embodiment, the engagement of trigger engagement members 1230 of ram assembly 122 with ram holding member 1042 causes a transfer of force from energy source 120 through to ram holding member 1042. In one embodiment, bulges 1230a are configured to bias such that exertion of force by bulges 1230a on ram holding member 1042 causes trigger engagement members 1230 to splay and exert a radial force on the wall of the opening of trigger member (e.g., opening 302 of floating trigger member 300 or opening 1408 of trigger member 1400). In one embodiment, the exertion of the radial force by trigger engagement members 1230 on the wall of the opening of the trigger member (e.g., opening 302 of floating trigger member 300 or opening 1408 of trigger member 1400) is such that it causes any movement of the trigger member (e.g., floating trigger member 300 or trigger member 1400) to be met with a friction force. In one embodiment, the factors that affect the amount of friction force between the trigger member and trigger engagement members 1230 include the amount of radial force being applied on the wall of the opening of the trigger member by trigger engagement members 1230 and the interaction between the contacting surfaces of the trigger engagement members 1230 and the wall of the opening of the trigger member. In one embodiment, generally, when holding all other variables constant, the greater the amount of radial force being applied on the wall of the opening of the trigger member by trigger engagement member 1230, the greater the frictional force generated by movement of the trigger member. In one embodiment, generally, when holding all other variables constant, the lower the amount of radial force being applied on the wall of the opening of the trigger member by trigger engagement member 1230, the lower the frictional force generated by movement of the trigger member. In one embodiment, to actuate injection device 100, the user must apply a force on the distal end of guard 106, which cause guard 106 to engage the trigger member (e.g., floating trigger member 300 or trigger member 1400) and actuate injection device 100. In one embodiment, the force being applied to the distal end of guard 106 must be sufficient to overcome the friction force caused by the contact between the trigger member and the trigger engagement members 1230.

The embodiments of designs where main spring force, in its compressed pre-fired state, acts on the restraining components in such a manner where the force of the compressed main spring is more axial than radial with the result of a potentially lower triggering force. This is especially important where the compressed forces of the main spring are high spring forces as described. In one embodiment, in a pre-fired state, bulges 1230a on trigger engagement member 1230, when engaged with ram holding member 1042, distribute both an axial force and a radial force on ram holding member 1042. However, in one embodiment, the bulges 1230a are configured to bias the forces toward a radial force directed on ram holding member 1042 by trigger engagement member 1230 to cause the trigger engagement members 1230 to splay outward and engage the wall of opening of trigger member (e.g., opening 302 of floating trigger member 300 or opening 1408 of trigger member 1400). In one embodiment, latch retention angle 172 determines the amount of axial force and radial force that is translated to the ram holding member 1042. In one embodiment, as latch retention angle 172 increases, less radial force is exerted on ram holding member 1042 by trigger engagement member 1230 and, thus, the frictional force resulting from the splaying of ram engagement members 1230 is decreased. In one embodiment, as the force acting to cause the splaying of trigger engagement member 1230 is decreased, less force is exerted on the wall of the opening of trigger member (e.g., opening 302 of floating trigger member 300 or opening 1408 of trigger member 1400) and, thereby, less force is required to actuate injection device 100 than in an embodiment having a larger latch retention angle 172. In one embodiment, where energy source 120 is a high force spring of about 19 lbs. load capacity and latch retention angle 172 is 40°, a user must overcome about 2.5 lbs., about 2.6 lbs., about 2.7 lbs., about 2.8 lbs. about 2.9 lbs. about 3.0 lbs, about 3.1 lbs, about 3.2 lbs. about 3.3 lbs., about 3.4 lbs., about 3.5 lbs., about 3.6 lbs., about 3.7 lbs., about 3.8 lbs., about 3.9 lbs., about 4.0 lbs., about 4.1 lbs., about 4.2 lbs., about 4.3 lbs., about 4.4 lbs., about 4.5 lbs., about 4.6 lbs., about 4.7 lbs., about 4.8 lbs., about 4.9 lbs., about 5.0 lbs., about 5.1 lbs., 5.2 lbs., about 5.3 lbs., about 5.4 lbs., about 5.5 lbs., about 5.6 lbs., about 5.7 lbs., about 5.8 lbs., about 5.9 lbs., about 6.0 lbs., about 6.1 lbs., about 6.2 lbs., about 6.3 lbs., about 6.4 lbs., about 6.5 lbs., about 6.6 lbs., about 6.7 lbs., about 6.8 lbs., about 6.9 lbs., about 7.0 lbs., about 7.1 lbs., about 7.2 lbs., about 7.3 lbs., about 7.4 lbs., about 7.5 lbs., about 7.6 lbs., about 7.7 lbs., about 7.8 lbs., about 7.9 lbs., about 8.0 lbs., about 8.1 lbs., about 8.2 lbs., about 8.3 lbs., about 8.4 lbs., about 8.5 lbs., about 8.6 lbs., about 8.7 lbs., about 8.8 lbs., about 8.9 lbs., about 9.0 lbs., about 9.1 lbs., about 9.2 lbs., about 9.3 lbs., about 9.4 lbs., about 9.5 lbs., about 9.6 lbs., about 9.7 lbs., about 9.8 lbs., about 9.9 lbs., about 10.0 lbs. or any range determinable from the preceding pounds (for example, about 2.5 lbs. to about 3.5 lbs. or about 3.4 lbs. to about 8.7 lbs.) of friction force to actuate injection device 100. In another embodiment, where energy source 120 is a high force spring with 18 lbs. load capacity and latch retention angle 172 is 80°, a user will need only overcome about 0.25 lbs, about 0.30 lbs, about 0.35 lbs, about 0.40 lbs, about 0.45 lbs, about 0.50 lbs, about 0.55 lbs, about 0.60 lbs, about 0.65 lbs, about 0.70 lbs, about 0.75 lbs, about 0.80 lbs, about 0.85 lbs, about 0.90 lbs, about 0.95 lbs, about 1.00 lbs, about 1.05 lbs, about 1.10 lbs, about 1.15 lbs, about 1.20 lbs, about 1.25 lbs, about 1.30 lbs, about 1.35 lbs, about 1.40 lbs, about 1.45 lbs, about 1.50 lbs, about 1.55 lbs, about 1.60 lbs, about 1.65 lbs, about 1.70 lbs, about 1.75 lbs, about 1.80 lbs, about 1.85 lbs, about 1.90 lbs, about 1.95 lbs, about 2.00 lbs, about 2.05 lbs, about 2.10 lbs, about 2.15 lbs, about 2.20 lbs, about 2.25 lbs, about 2.30 lbs, about 2.35 lbs, about 2.40 lbs, about 2.45 lbs, about 2.50 lbs, about 2.55 lbs, about 2.60 lbs, about 2.65 lbs, about 2.70 lbs, about 2.75 lbs, about 2.80 lbs, about 2.85 lbs, about 2.90 lbs, about 2.95 lbs, about 3.00 lbs, about 3.05 lbs, about 3.10 lbs, about 3.15 lbs, about 3.20 lbs, about 3.25 lbs, about 3.30 lbs, about 3.35 lbs, about 3.40 lbs, about 3.45 lbs, about 3.50 lbs, about 3.55 lbs, about 3.60 lbs, about 3.65 lbs, about 3.70 lbs, about 3.75 lbs, about 3.80 lbs, about 3.85 lbs, about 3.90 lbs, about 3.95 lbs, about 4.00 lbs, about 4.05 lbs, about 4.10 lbs, about 4.15 lbs, about 4.20 lbs, about 4.25 lbs, about 4.30 lbs, about 4.35 lbs, about 4.40 lbs, about 4.45 lbs, about 4.50 lbs, about 4.55 lbs, about 4.60 lbs, about 4.65 lbs, about 4.70 lbs, about 4.75 lbs, about 4.80 lbs, about 4.85 lbs, about 4.90 lbs, about 4.95 lbs, about 5.00 lbs, or any range determinable from the preceding pounds (for example, about 0.25 lbs. to about 1.15 lbs. or about 2.10 lbs. to about 3.80 lbs.) of friction force to actuate injection device 100.

Table 3 shows exemplary force values needed to overcome the friction force to actuate injection device 100 where the energy source 120 is a high force spring with 18 lbs. load capacity and the latch retention angle 172 is 80° (Design A) and 40° (Design B).

TABLE 3

| Test | Trigger Force Design A (in lbs) | Trigger Force Design B (in lbs) |
| --- | --- | --- |
| 1 | 1.01 | 3.50 |
| 2 | 0.95 | 3.80 |
| 3 | 1.00 | 2.90 |
| 4 | 0.96 | 4.00 |
| 5 | 1.07 | 3.20 |
| Average | 1.00 | 3.48 |

In certain embodiments, a user will need to overcome both the friction force and the force resiliently biasing guard 106 toward the extended position via spring 114 to actuate injection device 100.

In certain embodiments, energy source 120 is configured to generate sufficient force to cause disengagement of bulges 1230a and trigger engagement member 1230 when trigger engagement members 1230 are no longer engaged with the wall of the opening of the trigger member (e.g., opening 302 of floating trigger member 300 or opening 1408 of trigger member 1400). In one embodiment, the minimum axial force needed to cause disengagement of bulges 1230a and trigger engagement member 1230 when trigger engagement members 1230 are no longer engaged with the wall of the opening of the trigger member (e.g., opening 302 of floating trigger member 300 or opening 1408 of trigger member 1400) is about 0.5 lbs., about 1.0 lbs., about 1.5 lbs., about 2.0 lbs., about 2.5 lbs., about 3.0 lbs., about 3.5 lbs., about 4.0 lbs., about 4.5 lbs., about 5.0 lbs., about 5.5 lbs., about 6.0 lbs., about 6.5 lbs., about 7.0 lbs., about 7.5 lbs., about 8.0 lbs., about 8.5 lbs., about 9.0 lbs., about 9.5 lbs., about 10.0 lbs., about 10.5 lbs., about 11.0 lbs., about 11.5 lbs., about 12.0 lbs., about 12.5 lbs., about 13.0 lbs., about 13.5 lbs., about 14.0 lbs., about 14.5 lbs., about 15.0 lbs., about 15.5 lbs., about 16.0 lbs., about 16.5 lbs., about 17.0 lbs., about 17.5 lbs., about 18.0 lbs., or any range determinable from the preceding loads (for example, about 2.5 lbs. to about 3.5 lbs. or about 8.5 lbs. to about 9.5 lbs.). In other embodiments, the minimum axial force needed to cause disengagement of bulges 1230a and trigger engagement member 1230 when members 1230 are no longer engaged with the wall of the opening of the trigger member (e.g., opening 302 of floating trigger member 300 or opening 1408 of trigger member 1400) is about 10%, about 15%, about 20%, about 25%, about 30%, about 35%, about 40%, about 45%, about 50%, about 55%, about 60%, about 65%, about 70% or any range determinable from the preceding percentages (for example, about 15% to about 20% or about 45% to about 55%) of the force generated by energy source 120 acting on ram assembly 122.

Figure 18:
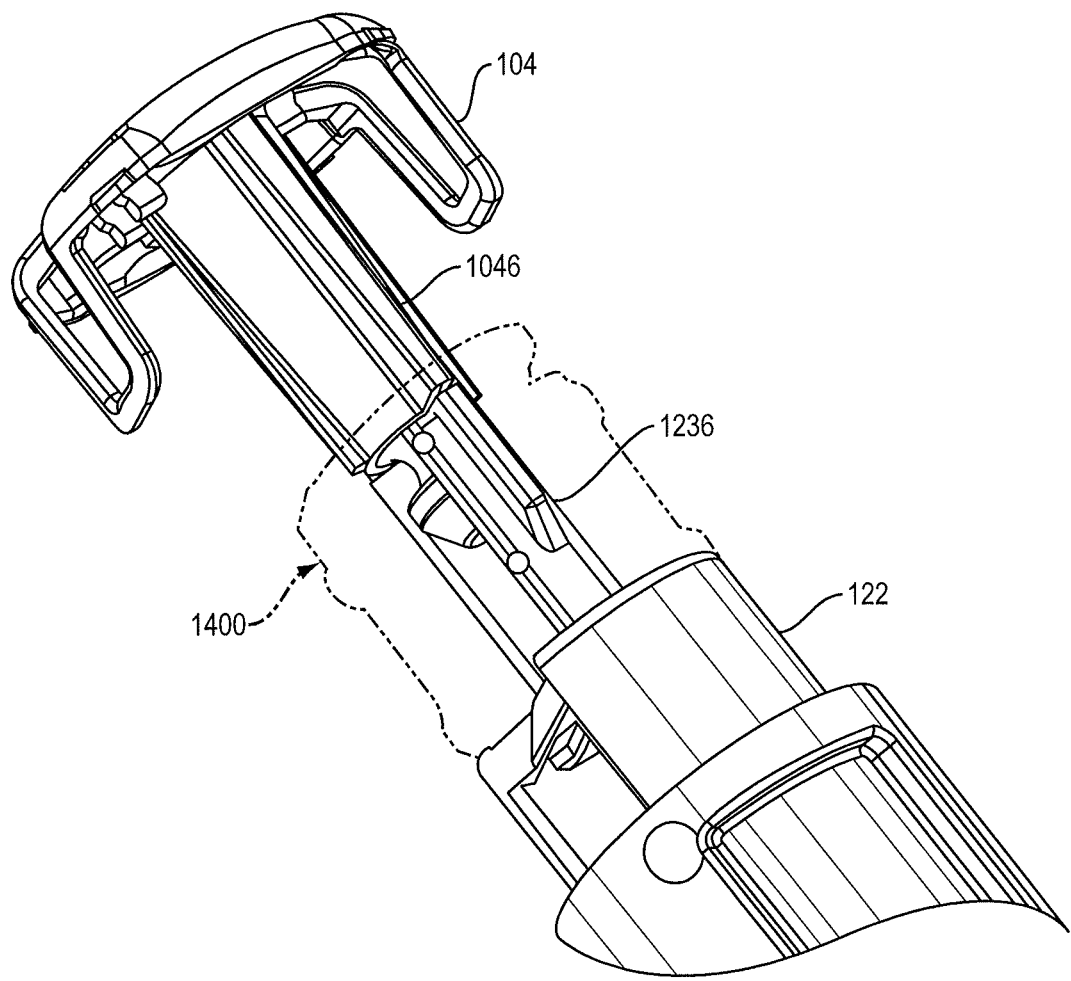
FIG. 18 shows a close-up view of an engagement of a trigger engagement member and a ram retaining member of an exemplary injection device according to an exemplary embodiment of the present disclosure.

In one embodiment, injection device 100 includes an anti-rotational mechanism that prevents ram assembly 122 from rotating relative to housing end/end cap 104. In one embodiment, the anti-rotational mechanism controls alignment of housing end/end cap 104 and ram assembly 122. In certain embodiments, improper alignment of the housing end/end cap and ram assembly will prevent the disengagement of ram assembly 122 from the housing end/end cap 104 or cause incomplete drug delivery. In one embodiment, as shown in FIG. 18, housing end/end cap 104 includes one or more anti-rotational ribs 1046. In other embodiments, ram assembly 122 has one or more anti-rotational ribs 1236. In one embodiment, in a pre-triggered, anti-rotational ribs 1046 of the housing end/end cap 104 align with anti-rotational ribs 1236 of ram assembly 122 within a groove 1412 of the trigger member 1400 such that ram assembly 122 is prevented from rotating relative to housing end/end cap 104.

In an exemplary embodiment, the injection device 100 can be in a pre-firing "safeties-on" configuration. For example, in the pre-firing "safeties-on" configuration, injection device 100 is in a pre-firing state and cap 200 is affixed to injection device 100. In this configuration, guard 106 is in the extended position under force of spring 114 covering needle 112, ram assembly 122 is in its proximal position, and energy source 120 has not released its energy. Further, in this state, trigger engagement members 1230 of ram assembly 122 are engaged with opening 302 of the floating trigger member 300 and aligned in the first position 302a (e.g., pre-firing condition) of opening 302. Further, trigger engagement members 1230 are also engaged with ram holding member 1042 of housing end/end cap 104. In this position, the trigger engagement member 1230 with ram holding member 1042 of housing end/end cap 104 oppose the force of energy source 120. Further, with trigger engagement members 1230 aligned within the first position 302a of opening 302, the retaining portion 306 of opening 302 prevents trigger engagement members 1230 from splaying open and disengaging ram holding member 1042 under the force of energy source 120.

In an exemplary embodiment, the injection device 100 can be in a pre-firing "ready-to-use" state. For example, in a pre-firing "ready-to-use" configuration, cap 200 has been removed, but the user has not otherwise initiated an injection. Accordingly, in this state, the medicament is still in medicament chamber 110, guard 106 remains in an extended position covering needle 112, energy source 120 has not released the energy that it has stored, and trigger engagement member 1230 of ram assembly 122 remain engaged with ram holding member 1042 and aligned in the first position (302a) of opening 302 of floating trigger member.

In an exemplary embodiment, the injection device 100 can be in a triggered or "just-fired" state. For example, in a triggered or "just-fired" state, guard 106 has been proximally slidably displaced (e.g., by application of a force on the distal end of guard 106) from the extended position to the retracted position, thereby exposing needle 112. Energy source 120 is just beginning to release its stored energy (e.g., the exemplary compression spring remains compressed), and ram assembly 122 remains in the proximal-most position. Injection device 100 may be in this state, for example, during an initial stage of use by a user. For example, this can be observed when the user has pressed guard 106 of injection device 100 against an injection site to perform an injection. Accordingly, the force exerted by the user in pressing guard 106 of injection device 100 against the injection site may have proximally displaced guard 106 against the force of spring 114, thereby displacing guard 106 into the retracted position and exposing needle 112 to penetrate the user's skin at the injection site.

In on embodiment, in this triggered state, guard 106 has been displaced into the retracted position, camming surfaces 1064 of guard 106 engage camming surfaces 308 of floating trigger member 300, thereby camming floating trigger member 300. This camming action rotates floating trigger member 300, causing trigger engagement members 1230 to become unaligned with the first position of opening 302 and become aligned with the second position of opening 302. In this position, trigger engagement members 1230 are no longer restrained from splaying open by retaining portion 306 of opening 302. Accordingly, trigger engagement members 1230 splay open under the force of, energy source 120, causing bulges 1230a to disengage with ram holding member 1042 of housing end/end cap 104. The disengagement of bulges 1230a with ram holding member 1042 allows ram assembly 122 to be distally slidably displaced relative to housing 102 under the force generated by energy source 120. In one embodiment, the distal displacement of ram assembly 120 is restrained by ram assembly 120 abutting a proximal surface of ring-like structure 1160 of sleeve 116.

In an exemplary embodiment, the injection device 100 can be in a "just-injected" state. This state follows the disengagement of bulges 1230a with ram holding member 1042 and the distal displacement of ram assembly 122 described above. In this state, energy source 120 (e.g., a compression spring) has released its energy, thereby distally displacing ram assembly 122. Further, guard 106 remains compressed in the retracted position. This state may be observed during use of injection device 100 immediately following the trigger or "just-used" state. As described above, camming of floating trigger member 300 aligns projections 1230 with the second position defined by opening 302, allowing trigger engagement members 1230 to splay open and disengage ram holding member 1042 under the force released by energy source 120. Accordingly, energy source 120 has released at least some, if not all, of its stored energy (e.g., compression spring is less compressed), and ram assembly 122, as well as ram 1232, has been distally displaced into a distal position. The distal displacement of ram 1232 urges plunger 118 in a distal direction, injecting the medicament into the user by dispensing the medicament in medicament chamber 110 through needle 112 and into the user. Although the injection has, in certain embodiments, been completed in this state, injection device 100 is still likely pressed against the injection site since guard 106 remains in a retracted position exposing needle 112. Further, in certain embodiments, this distal displacement of ram assembly 122 positions ram assembly 122 such that it is displayed in a window of housing 102. In an exemplary embodiment, after the distal displacement of ram assembly 122, it is disposed between medicament container 110 and housing 102 such that it is entirely occluding the window so that only ram assembly 122 is visible through the window, and medicament container 110 is no longer visible (e.g., ram assembly is disposed between medicament container 110 and the window). Further, ram assembly 122 can have a color (as described above) that would be a clear indicator to a user that injection device 100 has been used, and different than the other colors visible from the outside of the injector before firing.

In an exemplary embodiment, the injection device can be in a "locked-out" state. For example, the "locked-out" state can be observed after the user has removed injection device 100 from the injection site. In this state, nothing is restraining guard 106 in the retracted position against the force of spring 114, and accordingly, guard 106 is distally displaced from the retracted position to the extended position under the force of spring 114, thereby covering needle 112. As guard 106 moves distally from the retracted position to the extended position under the force of spring 114, projections 1066, which are disposed on springs 1068 biased in an outward direction, engage the openings created between proximal surfaces of legs 1170 of sleeve 116 and proximal walls of openings 1226. Accordingly, the association of projections 1066 with the proximal walls of openings 1226 prevents guard 106 from being displaced proximally, and the association of projections 1066 with the proximal surfaces of legs 1170 prevents guard 106 from being displaced distally. Thus, guard 106 is in a locked position, thereby locking-out injection device 100 such that needle 112 is covered and guard 106 is locked in place so that a user cannot attempt a subsequent injection. Afterwards, the user may affix cap 200 back onto the distal end of injection device 100.

Advantageously, in one embodiment, this "locked-out" state is not dependent on displacement of guard 106, but rather, is dependent on dispensing of the medicament stored in medicament chamber 110 and/or movement of ram assembly 122. For example, injection device 100 becomes locked-out in situations where the medicament is inadvertently dispensed, even if guard 106 has not been displaced. Injection device 100 can become locked-out in any instance where energy source 120 is activated and ram assembly 122 is distally displaced, causing ram 1232 to displace plunger 118, thereby dispensing the medicament in medicament chamber 110.

Figure 12:
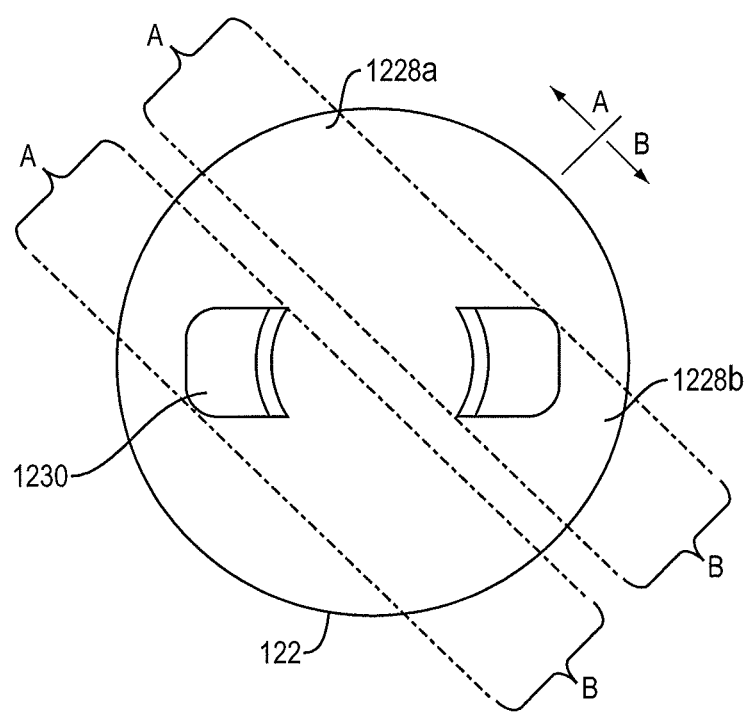
FIG. 12 shows a top view of a ram assembly of an exemplary injection device according to an exemplary embodiment of the present disclosure.

In an exemplary embodiment, many of the components of injection device 100 are made of a resilient plastic or polymer, or a metal. In one embodiment, projections 1230 of ram assembly 122 are oriented so that ram assembly 122 can be molded using a single mold. For example, as shown in FIG. 10, projections 1230 (which are in certain embodiments concentrically symmetrical to each other) can be aligned at an angle relative to the alignment of the other features of ram assembly 122, such as legs 1228 (which are in certain embodiments concentrically symmetrical to each other). For example, as shown in FIG. 12, a single mold can form the portion of ram assembly 120 designated A (including all the features, components, openings, etc. 1228A), and a single mold can form the portion of ram assembly designated B (including all the features, components, openings, etc. 1228B). Thus, in certain embodiments, each surface of projections 1230 is accessible along a direction of separating the two molds, and the two molds can be separated linearly without a concave portion of projections 1230 facing orthogonal to the separation direction impeding separation and removal of the molds.

Further, cap 200 can be configured helically so that it can be molded without a hole/opening. For example, cap 200 can include threads 206 that permit cap 200 to be threadedly removed from a mold. Further, outer housing 102 can include a translucent material to allow users to view the inner workings of injection device 100, and ascertain if it is malfunctioning (e.g., as shown in FIG. 1). Additionally, injection device 100 can include various gripping elements, such as ridges, pads, contours, or the like, to make injection device 100 more ergonomic, easy to use, and comfortable to the user. Further, injection device 100 can include markings, such as a sticker, brand markings, drug information, numerals, arrows, or the like, to indicate the steps needed to perform an injection, and areas for promotional markings such as brand and logo designations.

Figure 14A:
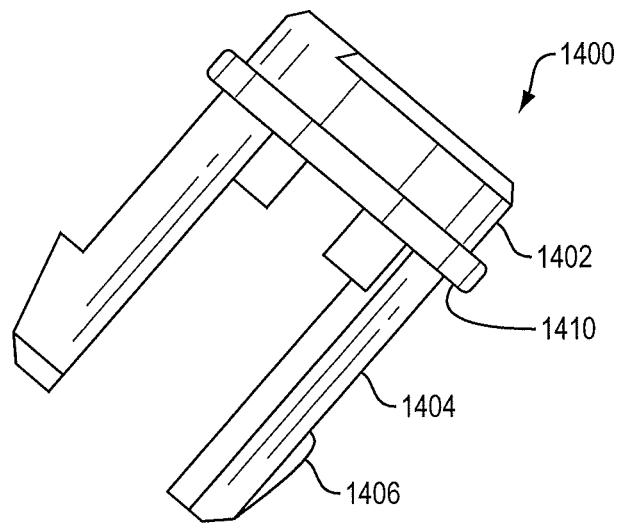
FIG. 14A is a perspective view of a trigger member of an exemplary injection device according to an exemplary embodiment of the present disclosure.
Figure 14B:
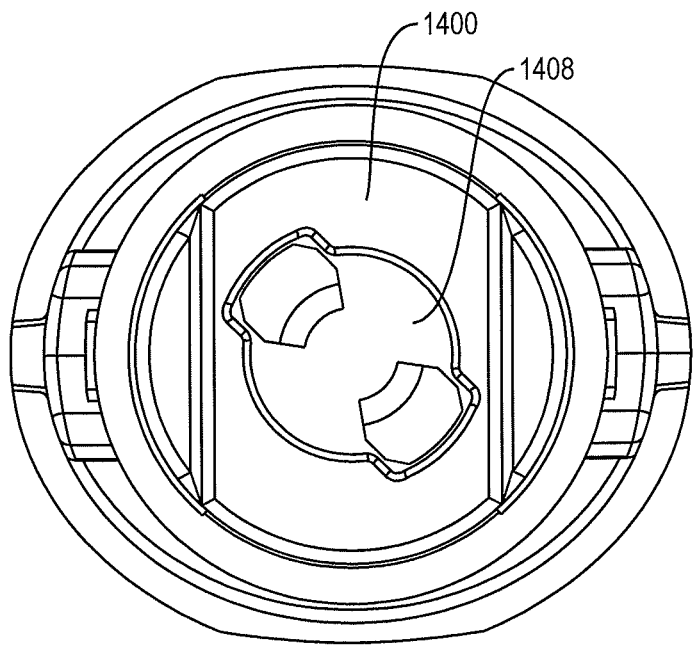
FIG. 14B is a cross-section view of an exemplary injection device according to an exemplary embodiment of the present disclosure.
Figure 14C:
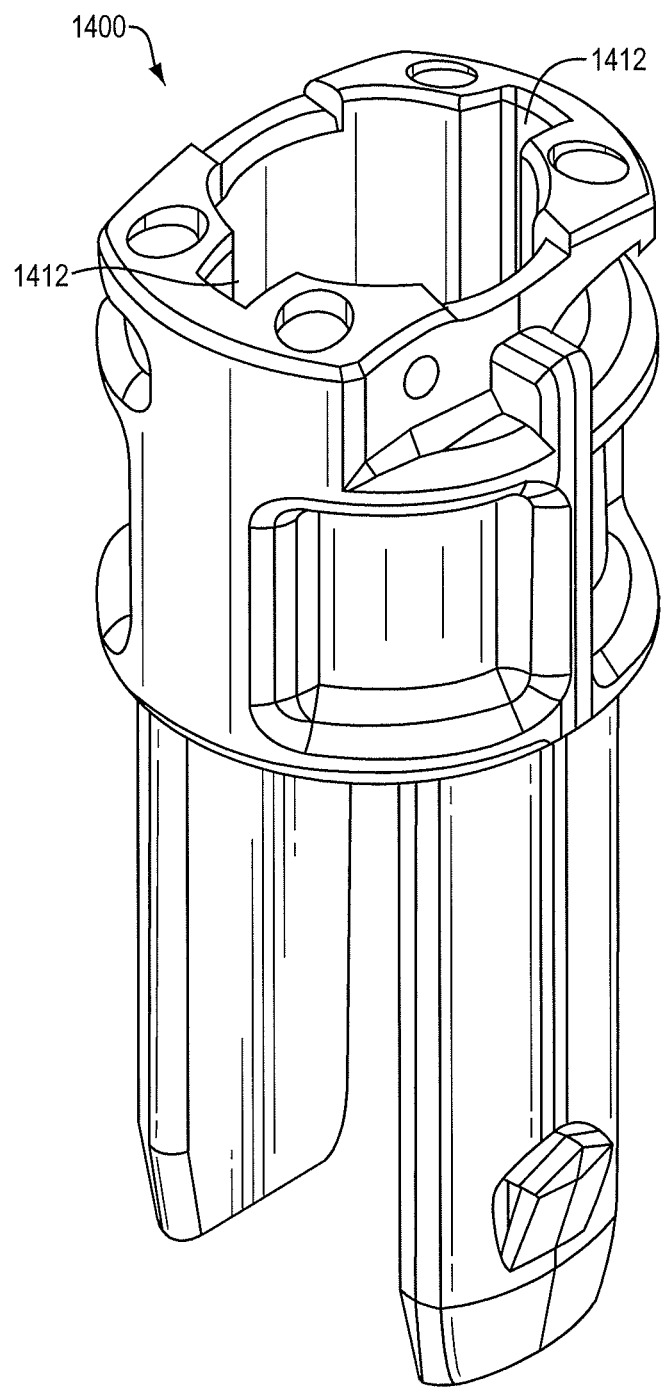
FIG. 14C is a perspective view of a trigger member of an exemplary injection device according to an exemplary embodiment of the present disclosure.

While illustrative embodiments of the invention are disclosed herein, it will be appreciated that numerous modifications and other embodiments may be devised by those skilled in the art. For example, the features for the various embodiments can be used in other embodiments. Other embodiments can include different mechanisms to cause the release of ram assembly 122 by actions on the trigger engagement member 1230 and a triggering member. For example, in one embodiment, the injection device 100 includes a trigger member 1400, as shown in FIGS. 14A and 14B. In one embodiment, the trigger member 1400 has a body 1402 and legs 1404 extending from the body 1402. In one embodiment, body 1402 includes lip 1410. In one embodiment, lip 1410 is configured to engage surface 1504 of guard 1500 (described in more detail below and as seen in FIG. 15D). In certain embodiments, legs 1402 have tabs 1406 extending from a distal end of legs 1404. In one embodiment, tabs 1406 are shaped and dimensioned to slideably engage guard 1500. Further, in one embodiment, trigger member 1400 includes an opening 1408 disposed through body 1402. In one embodiment, opening 1408 is configured to engage a trigger engagement member 1230 of firing mechanism 108. In one embodiment, engagement of bulges 1230a on trigger engagement member 1230 prevent injection device from firing. In one embodiment, trigger member 1400 is configured such that axial movement in a proximal direction causes disengagement of opening 308 and projections 1230. FIG. 14J shows another embodiment of trigger member 1400. In certain embodiments, trigger member 1400 includes a groove 1412 as part of an anti-rotational mechanism.

Figure 16A:
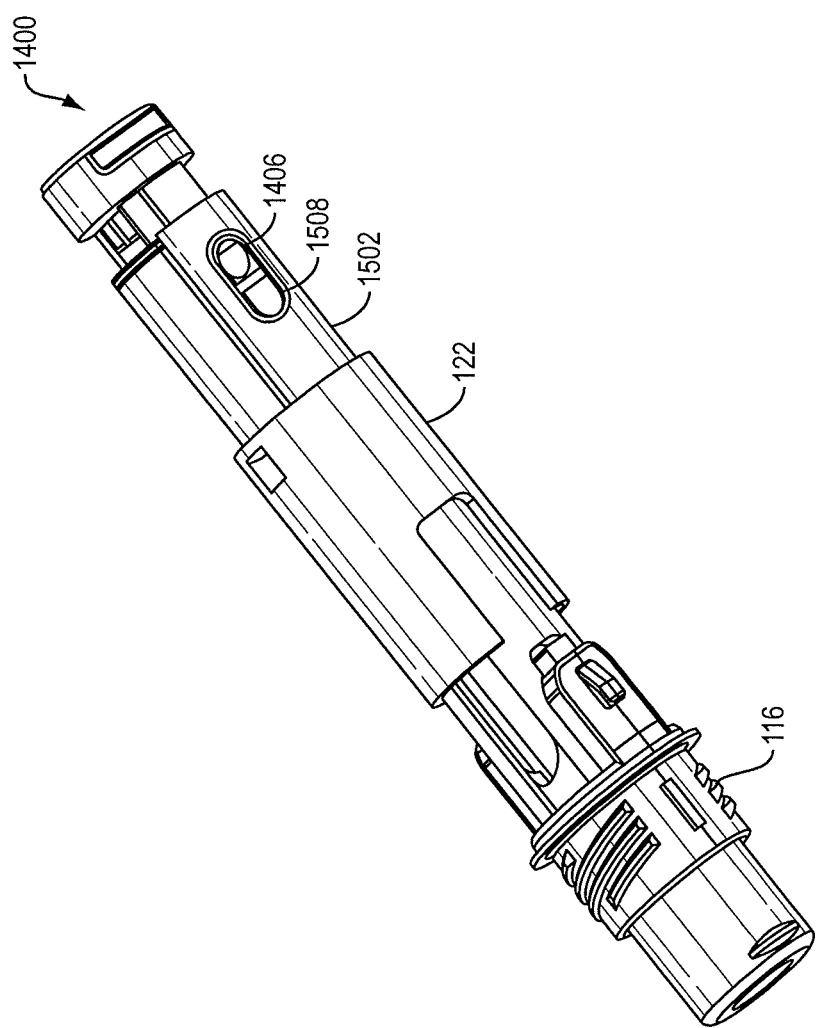
FIGS. 16A, 16B and 16C are various side views of an exemplary injection device according to an exemplary embodiment of the present disclosure in pre-triggered, triggering, and triggered positions, respectively.
Figure 16B:
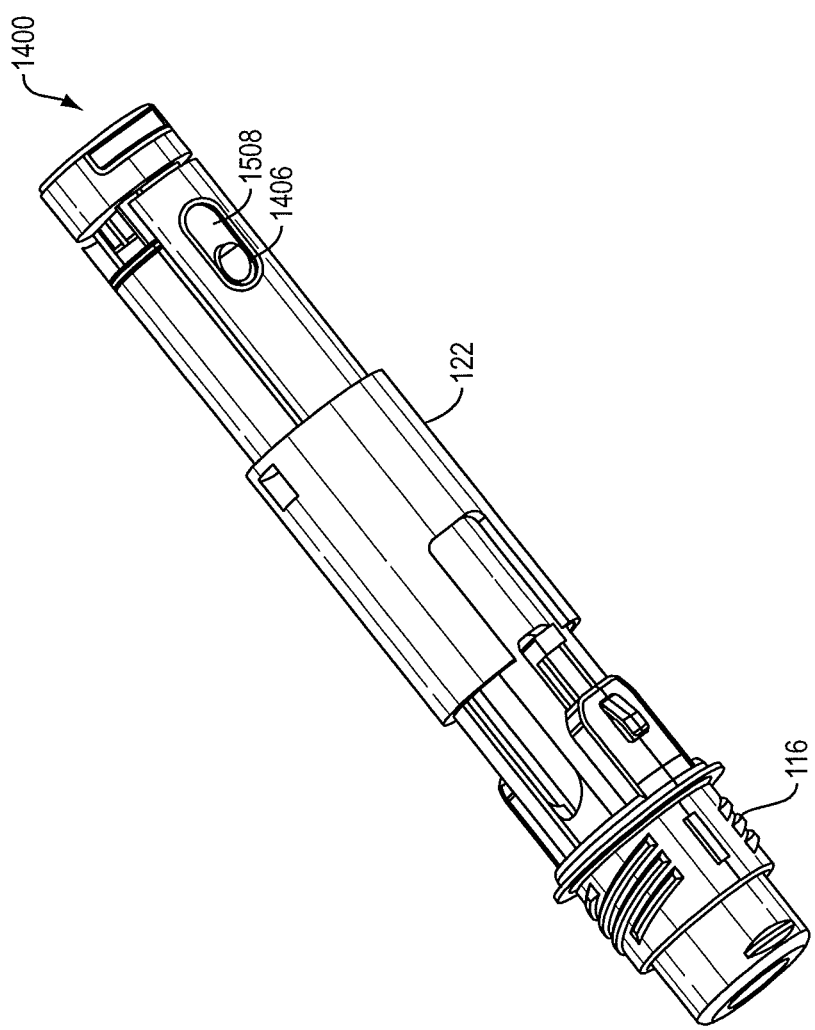
Figure 16C:
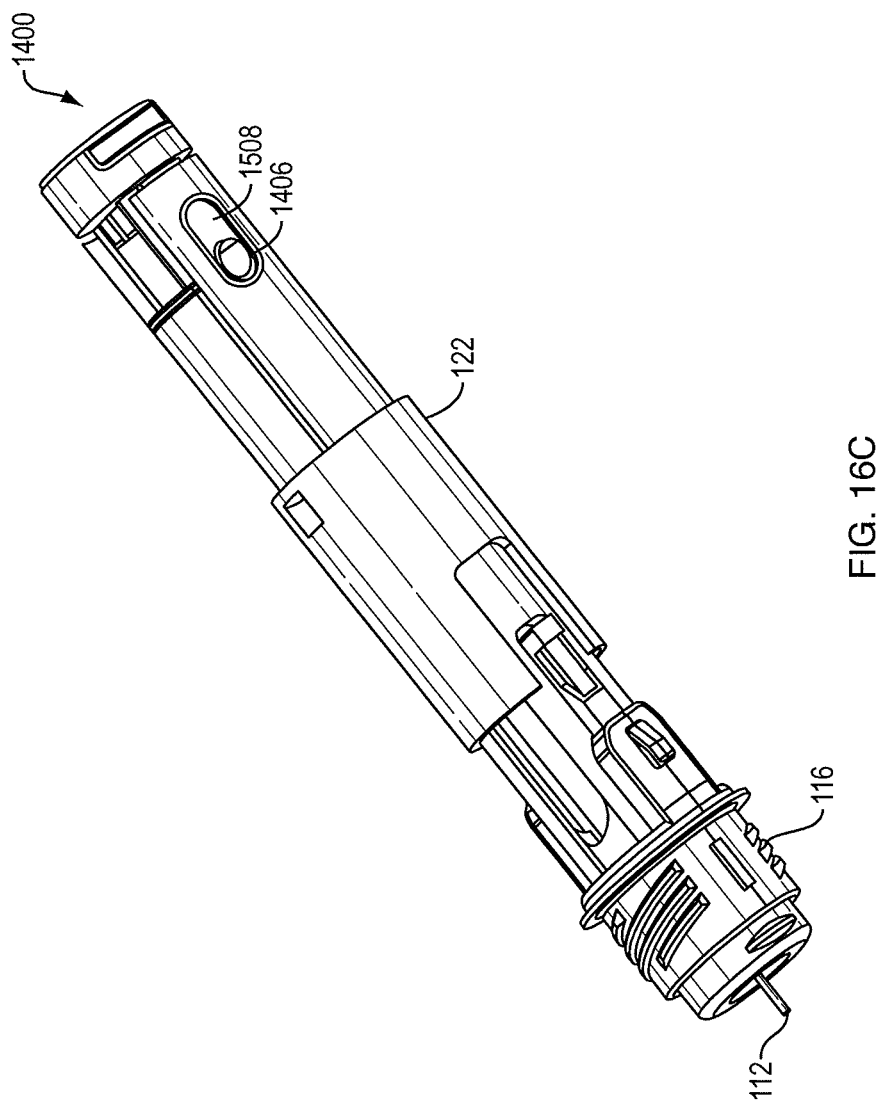
Figure 17D:
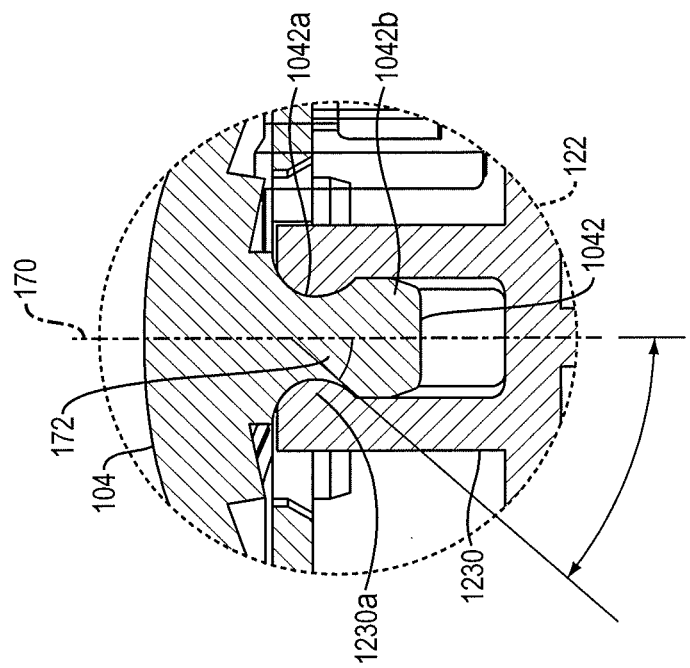
FIG. 17D is a magnified cross-section view of the end cap, ram assembly and trigger of the injection device shown in FIG. 17C.
Figure 17C:
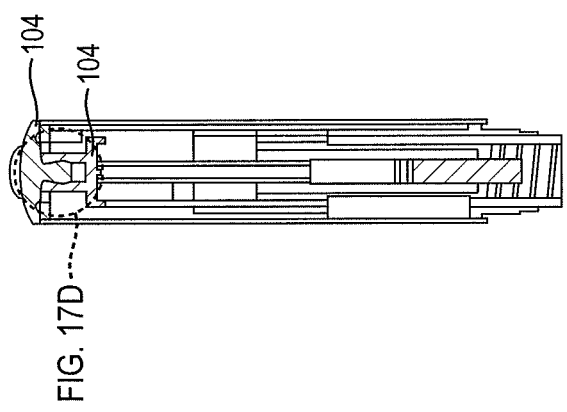
FIG. 17C is a cross-section view of the end cap, ram assembly and trigger of the injection device shown in FIG. 1.

As shown in FIGS. 15A through 15H, in one embodiment, injection device 100 includes a guard 1500. In one embodiment, guard 1500 includes legs 1502. In another embodiment, legs 1502 have firing-initiation members, such as surfaces 1504 at a proximal end of legs 1500. In one embodiment, surfaces 1504 are configured to engage lip 1410 of trigger member 1400. In one embodiment, legs 1502 are configured to be received in openings 1178 of ring-like structure 1160. In one embodiment, legs 1502 include ridges 1506 configured to engage grooves 1164a of sleeve 116, to facilitate alignment and guiding of legs 1502 as guard 1500 is axially displaced. In an exemplary embodiment, legs 1502 and surfaces 1504 are concentrically symmetrical. In one embodiment, surfaces 1504 are configured to engage firing mechanism 108 in initiating a firing of injection device 100 and performing an injection of the medicament stored in medicament chamber 110. In one embodiment, surfaces 1504 are shaped to engage lip 1410 of trigger member 1400 when guard 1500 is displaced from the extended position to the retracted position. In one embodiment, legs 1502 include apertures 1508. In one embodiment, apertures 1508 are sized and shaped to engage tabs 1406 of trigger member 1400. In one embodiment, apertures 1508 are sized and shaped to allow tabs 1406 to be slideably engageable with apertures 1508. In one embodiment, as shown in FIGS. 16A and 16B, when apertures 1508 and tabs 1406 are in a slideably engageable configuration, for a predetermine distance, guard 1500 can axially translate without movement of trigger member 300. In another embodiment, as shown in FIGS. 16A, 16B, and 16C, when apertures 1508 and tabs 1406 are in a slideably engageable configuration, after guard 1500 axially translates a predetermine distance without causing movement of trigger member 1400, axial translation of guard 1500 beyond the predetermined distance causes axial translation of trigger member 1400.

In one embodiment, apertures 1508 are sized and shaped to allow tabs 1406 to snap-fit within the aperture 1508. In one embodiment, when the apertures 1508 and tabs 1406 are in a snap-fit configuration, axial translation of guard 1500 causes direct axial translation of trigger member 1400 such that guard 1500 cannot axially translate without also translating trigger member 1400. In one embodiment, direct axial translation of trigger member 1400 in a proximal direction causes disengagement of opening 1408 of trigger member 1400 and trigger engagement members 1230 of firing mechanism, which causes disengagement of bulges 1230a and ram holding member 1042. In one embodiment, disengagement of ram holding member 1042 housing end/end cap 104 and trigger engagement members 1230 causes injections device 100 to fire.

Although not shown, it is also contemplated that a tab or protrusion can be located on legs 1502 of guard 1500 such that the tab can communicate, either slidingly or directly with an aperture located on trigger member 1400.

Other embodiments can include different mechanisms to cause the release of trigger engagement members 1230 from a trigger member, such as by direct rotation of the floating trigger member 300 by a user, such as via a slide or other element accessible on the outside of the housing, or by a button that is pushed with a finger, or another transmission mechanism to rotate the floating trigger member. Therefore, it will be understood that the appended claims are intended to cover all such modifications and embodiments that come within the spirit and scope of the present invention.

Each and every reference herein is incorporated by reference in its entirety. The entire disclosure of U.S. Pat. Nos. 8,496,619, 8,021,335, 7,776,015, and 6,391,003, U.S. Patent Pat. Application Nos. 2013/0303985, 2013/0331788, 2013/0317431, U.S. patent application Ser. No. 13/184,229 and U.S. provisional patent application Nos. 61/621,298 and 61/643,845 are hereby incorporated herein by reference thereto as if fully set forth herein. The term "about," as used herein, should generally be understood to refer to both the corresponding number and a range of numbers. Moreover, all numerical ranges herein should be understood to include each whole integer within the range.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

The invention claimed is:

1. An injector, comprising:
 a container containing progesterone or a derivative thereof;
 a trigger mechanism including:
  a trigger member disposed about an axis, the trigger member having a trigger member opening wall and a trigger member protrusion, and
  a ram assembly having a ram configured to pressurize the container for expelling the progesterone or derivative thereof from the container, the ram assembly further having a trigger engagement member configured to engage the trigger member opening wall when the trigger member is in a pre-firing condition;
 an energy source associated with the ram and configured to power the ram to expel the progesterone or derivative thereof; and
 a guard including a guard aperture receiving the trigger member protrusion, the guard configured to cause an axial translation of the trigger member in a proximal direction from the pre-firing condition to a firing condition in which the trigger engagement member is disengaged from the trigger member opening wall to allow the energy source to fire the ram.

2. The injector of claim 1, wherein the guard aperture slidingly receives the trigger member protrusion.

3. The injector of claim 1, wherein the injector is configured to inject at least about 0.5 ml of the progesterone or derivative thereof in less than about 14 seconds.

4. The injector of claim 1, wherein the energy source is configured to pressurize the progesterone or derivative thereof to a pressure within a range of about 90 p.s.i. to about 600 p.s.i.

5. The injector of claim 1, further comprising:
 an injector housing,
 wherein the guard includes a skin-contacting portion disposed at a distal end of the injector, the skin-contacting portion being movable proximally with respect to the housing when a force is applied to the skin-contacting portion at the distal end of the injector, the guard being associated with the trigger member and configured to cause the axial translation of the trigger member in a proximal direction from the pre-firing condition to the firing condition upon a proximal movement of the skin-contacting portion with respect to housing.

6. The injector of claim 5, wherein the skin-contacting portion is coupled to the guard, the guard being configured to expose a needle connected to the container upon the proximal movement of the skin-contacting portion.

7. The injector of claim 6, further comprising a needle in fluid communication with the container for injecting the progesterone or derivative thereof expelled therefrom when the ram is fired.

8. The injector of claim 7, wherein the energy source and needle are configured for injecting the progesterone or derivative thereof at an average velocity of at least about 1,000 cm/sec within the needle.

9. The injector of claim 1, further comprising a ram holding member that engages the trigger engagement member to axially retain the ram assembly in a proximal position against action of the energy source in the pre-firing condition.

10. The injector of claim 9, wherein in the firing condition the ram assembly is disengaged from the trigger member opening wall, and the energy source overcomes the engagement between the trigger engagement member and the ram holding member.

11. The injector of claim 9, wherein the ram holding member includes a projection that includes a bulge and a groove that are configured to engaged the trigger engagement member, and the trigger member opening wall retains the engagement of the trigger engagement member with the bulge and groove in the pre-firing condition.

12. The injector of claim 9, further comprising a latch retention angle defined by the axis and a contact surface of the ram holding member and the trigger engagement member.

13. The injector of claim 12, wherein the latch retention angle is between about 35° and about 45°.

14. The injector of claim 12, wherein the latch retention angle is between about 75° and about 85°.

15. An injector, comprising:
a container containing progesterone or an analogue of progesterone;
a trigger mechanism including:
a trigger member disposed about an axis, the trigger member having a trigger member opening wall and a trigger member protrusion, and
a ram assembly having a ram configured to pressurize the container for expelling the progesterone or analogue of progesterone from the container, the ram assembly further having a trigger engagement member configured to engage the trigger member opening wall when the trigger member is in a pre-firing condition;
an energy source associated with the ram and configured to power the ram to expel the progesterone or analogue of progesterone; and
a user-operable guard including a guard aperture receiving with the trigger member protrusion, the user-operable guard configured to cause an axial translation of the trigger member in a proximal direction from the pre-firing condition to a firing condition in which the trigger engagement member is disengaged from the trigger member opening wall to allow the energy source to fire the ram,
wherein the energy source expels the analogue of progesterone at a stream velocity of at least about 100 centimeters per second.

* * * * *